United States Patent
Fujimoto et al.

(10) Patent No.: US 9,366,680 B2
(45) Date of Patent: Jun. 14, 2016

(54) METHOD FOR EVALUATING MYOCARDIAL ISCHEMIC STATE USING BLOOD SAMPLE

(75) Inventors: Hirotaka Fujimoto, Kyoto (JP); Toru Suzuki, Tokyo (JP)

(73) Assignees: SHIMADZU CORPORATION, Kyoto (JP); THE UNIVERSITY OF TOKYO, Tokyo (JP)

( * ) Notice: Subject to any disclaimer, the term of this patent is extended or adjusted under 35 U.S.C. 154(b) by 631 days.

(21) Appl. No.: 13/060,552

(22) PCT Filed: Aug. 28, 2008

(86) PCT No.: PCT/JP2008/065444
§ 371 (c)(1),
(2), (4) Date: Feb. 24, 2011

(87) PCT Pub. No.: WO2010/023749
PCT Pub. Date: Mar. 4, 2010

(65) Prior Publication Data
US 2011/0151583 A1    Jun. 23, 2011

(51) Int. Cl.
*C07K 16/26* (2006.01)
*G01N 33/68* (2006.01)
*G01N 33/74* (2006.01)
*G01N 33/543* (2006.01)

(52) U.S. Cl.
CPC ............ *G01N 33/6893* (2013.01); *C07K 16/26* (2013.01); *G01N 33/543* (2013.01); *G01N 33/74* (2013.01); *C07K 2317/34* (2013.01); *G01N 2333/58* (2013.01); *G01N 2800/32* (2013.01)

(58) Field of Classification Search
CPC .. C07K 16/26; C07K 2317/34; G01N 33/543; G01N 33/6893; G01N 33/74; G01N 2333/58; G01N 2800/32
USPC .............. 435/7.1, 7.94; 436/501, 518, 86, 87, 436/175; 530/387.9, 388.24, 389.2, 391.1
See application file for complete search history.

(56) References Cited

U.S. PATENT DOCUMENTS

2005/0064511 A1    3/2005    Buechler et al.

FOREIGN PATENT DOCUMENTS

JP        2007-322187 A      12/2007
WO      WO-2006/029369 A2    3/2006
WO      WO-2006/087373 A1    8/2006

OTHER PUBLICATIONS

Shimizu et al., 2002. Molecular forms of huam brain natriuretic peptide in plasma. Clinica Chimica Acta 316: 129-135.*
International Preliminary Report on Patentability for Application No. PCT/JP2008/065444 mailed Mar. 10, 2011.
Supplementary European Search Report for the Application No. EP 08 80 9519 dated Nov. 24, 2011.
Bruins, Sanne et al., "High Intraindividual Variation of B-Type Natriuretic Peptide (BNP) and Amino-Terminal proBNP in Patients with Stable Chronic Heart Failure", Clinical Chemistry, 2004, vol. 50, No. 11, pp. 2052-2058.

* cited by examiner

*Primary Examiner* — Gail R Gabel
*Assistant Examiner* — James L Grun
(74) *Attorney, Agent, or Firm* — Cheng Law Group, PLLC

(57) ABSTRACT

The present invention provides a method and an index capable of less-invasively determining myocardial ischemia such as ischemic heart disease or restenosis after percutaneous coronary intervention. The present invention also provides an index that allows the cardiovascular disease other than heart failure to be determined even from a blood sample showing a BNP value from which the cardiovascular disease other than heart failure cannot be determined by a conventional method. A method for determining myocardial ischemia comprising subjecting a blood sample which is derived from a test subject and which contains a BNP molecular group containing at least two selected from the group consisting of BNP 1-32 molecule, BNP 3-32 molecule, BNP 4-32 molecule, BNP 5-32 molecule, and a molecule having a mass number larger than that of BNP 5-32 molecule by 16 Da to a detection process capable of distinguishing and quantifying the individual BNP molecules different in mass number to detect the BNP molecular group, wherein myocardial ischemia in the test subject is determined using, as an index, a ratio between a detected intensity of at least one molecule selected from the BNP molecular group and a detected intensity of at least one other molecule selected from the BNP molecular group.

6 Claims, 16 Drawing Sheets

SEQUENCE LISTING

```
<160> NUMBER OF SEQ ID NOS: 4

<210> SEQ ID NO 1
<211> LENGTH: 32
<212> TYPE: PRT
<213> ORGANISM: Homo sapiens

<400> SEQUENCE: 1

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 2
<211> LENGTH: 30
<212> TYPE: PRT
<213> ORGANISM: Homo sapiens

<400> SEQUENCE: 2

Lys Met Val Gln Gly Ser Gly Cys Phe Gly Arg Lys Met Asp Arg Ile
1               5                   10                  15

Ser Ser Ser Ser Gly Leu Gly Cys Lys Val Leu Arg Arg His
            20                  25                  30

<210> SEQ ID NO 3
<211> LENGTH: 29
<212> TYPE: PRT
<213> ORGANISM: Homo sapiens

<400> SEQUENCE: 3

Met Val Gln Gly Ser Gly Cys Phe Gly Arg Lys Met Asp Arg Ile Ser
1               5                   10                  15

Ser Ser Ser Gly Leu Gly Cys Lys Val Leu Arg Arg His
            20                  25

<210> SEQ ID NO 4
```

```
<211> LENGTH: 28
<212> TYPE: PRT
<213> ORGANISM: Homo sapiens

<400> SEQUENCE: 4

Val Gln Gly Ser Gly Cys Phe Gly Arg Lys Met Asp Arg Ile Ser Ser
1               5                   10                  15

Ser Ser Gly Leu Gly Cys Lys Val Leu Arg Arg His
            20                  25
```

METHOD FOR EVALUATING MYOCARDIAL ISCHEMIC STATE USING BLOOD SAMPLE

TECHNICAL FIELD

The present invention relates to the fields of diagnostic medicine, diagnostic testing equipment, cardiovascular internal medicine, comprehensive medical examination, and mass spectrometry. More specifically, the present invention relates to a method for assessing myocardial ischemia using a blood sample.

BACKGROUND ART

At clinical sites around the world including Japan, diagnosis of heart failure is widely performed by measuring the blood levels of B-type natriuretic hormone (BNP) that is a hormone secreted mainly by cardiac myocyte. All over the world, it has been verified that there is a very strong correlation between the blood levels of BNP and the severity of chronic heart failure, and therefore BNP is the only biomarker currently used to assess the severity of heart failure.

A method for diagnosis of heart failure used at clinical sites has been almost established. More specifically, the blood levels of BNP are measured by an immunochemical method such as EIA or ELISA, and when the levels of BNP are 100 pg/mL or higher or 150 pg/mL or higher, a diagnosis of "suspected heart failure" is generally made. On the other hand, when the levels of BNP are equal to or less than 18.4 pg/mL that is the upper limit of the reference value of BNP, a diagnosis of "nothing abnormal detected" is generally made, and when the levels of BNP are in the range between thresholds (more specifically, 18.4 pg/mL to 100 pg/mL or 18.4 pg/mL to 150 pg/mL), there is a general clinical suspicion of some kind of cardiovascular disease, and therefore a diagnosis of "follow-up required and, if necessary, further examination" is made.

Among cardiovascular diseases, ischemic heart disease is clinically diagnosed by an outpatient examination such as electrocardiography, exercise electrocardiography, or echocardiography. However, it is difficult to completely detect ischemic heart disease by such an examination, and therefore it is usually necessary to perform a cardiac catheterization test requiring hospital admission for accurate diagnosis.

As nondrug treatment of ischemic heart disease, surgery to widen a stenotic area in the coronary artery is generally performed. An example of such surgery widely performed includes percutaneous coronary intervention (PCI). It is conventionally known that restenosis of a widened vessel occurs in about 20 to 40% of patients who underwent PCI within 3 to 6 months after PCI. However, in recent years, the frequency of restenosis has been reduced to as low as 10% or less by using a drug-eluting stent (DES) in this surgery.

On the other hand, U.S. Pat. No. 7,341,838 and JP-T-2006-527190 have recently disclosed a method for classifying a disease state of a test sample by specifically measuring the amount of at least one BNP polypeptide selected from the group consisting of BNP 79-108, BNP 77-106, BNP 39-86, BNP 53-85, BNP 66-98, BNP 30-106, BNP 11-107, BNP 9-106, BNP 69-100, BNP 76-107, BNP 69-108, BNP 80-108, BNP 81-108, BNP 83-108, BNP 30-103, BNP 3-108, and BNP 79-106 (herein, a BNP precursor composed of 108 amino acids is expressed as BNP 1-108, based on which these BNP polypeptides are expressed) contained in the test sample. More specifically, these documents describe that BNP 3-108 may distinguish unstable angina or myocardial infarction from congestive heart failure, which is based on the result of analysis of test samples derived from a patient having a BNP value of 353.5 pg/mL and from a patient having a BNP value of 905.5 pg/mL.

Further, JP-A-2007-322187 has recently disclosed a method for measuring the blood levels of modified low-density lipoprotein (modified LDL) as an example of a method for assessing the risk of development of restenosis after PCI.

Patent Document 1: U.S. Pat. No. 7,341,838
Patent Document 2: JP-T-2006-527190
Patent Document 3: JP-A-2007-322187

DISCLOSURE OF THE INVENTION

Problems to be Solved by the Invention

The diagnosis of heart failure by measurement of blood levels of BNP are clinically effective. However, under the present circumstances, a method of diagnosing ischemia by measurement of blood levels of BNP has not been established. Further, when the blood levels of BNP are within the range between thresholds for determining whether there is suspicion of heart failure (more specifically, 18.4 pg/mL to 100 pg/mL or 18.4 pg/mL to 150 pg/mL), only a diagnosis that there is suspicion of some kind of cardiovascular disease is made and its actual condition is not clear. That is, when the blood levels of BNP are within the range between the above-mentioned thresholds, it is impossible to assess cardiovascular disease under the present circumstances.

As one of examinations currently used for diagnosis of ischemic heart disease among cardiovascular diseases, exercise electrocardiography can be mentioned. However, the sensitivity and specificity of exercise electrocardiography are both about 70%, and therefore diagnostic reliability is not so high. Further, in the case of this examination, a test subject needs to do exercise, which places a heavy burden on a patient. Further, elderly people with weak legs or with troubles in leg joints cannot undergo this examination. During this examination, a doctor needs to always observe a test subject, but there is a possibility that a cardiovascular event is caused by exercise stress. In addition, this examination is contraindicated in people suspected to have, for example, unstable angina.

As described above, the frequency of restenosis after PCI has been reduced, but restenosis still occurs at a certain frequency. Therefore, an examination for diagnosis of the presence or absence of restenosis is still necessary. More specifically, a cardiac catheterization test is widely performed. However, a cardiac catheterization test is invasive and places a heavy burden on patients. Therefore, it is practically impossible to frequently perform a cardiac catheterization test. In addition, a cardiac catheterization test uses a contrast agent, and therefore the kidney toxicity of a contrast agent is a problem particularly for patients with kidney dysfunction.

On the other hand, as described above, U.S. Pat. No. 7,341,838 and JP-T-2006-527190 describe that BNP 3-108 may distinguish unstable angina or myocardial infarction from congestive heart failure, which is, however, based on the analytical result of test samples derived from a patient having a BNP value of 353.3 pg/mL and from a patient having a BNP value of 905.5 pg/mL. Further, these documents do not describe any significant difference in the detected levels of a specific BNP peptide between a test specimen derived from a patient having cardiovascular disease to be evaluated and a control specimen. That is, there is no description about an index useful for assessing cardiovascular disease.

Further, these documents describe that a test specimen derived from a patient having a low BNP value (more specifically, 39.6 pg/mL) was also analyzed in the same manner as in the analysis of the above-mentioned test specimens. However, in the case of such a patient having a low BNP value, a specific BNP peptide was not detected, and therefore no information was obtained.

It is therefore an object of the present invention to provide a method capable of less-invasively assessing myocardial ischemia (e.g., ischemic heart disease or restenosis).

It is also an object of the present invention to provide an index that allows the presence or absence of cardiovascular disease other than heart failure, especially myocardial ischemia, to be determined even from a blood sample showing a BNP value from which the presence or absence of cardiovascular disease including heart failure cannot be determined by a conventional method (i.e., a BNP value within the range between thresholds for determining whether there is suspicion of heart failure (more specifically, 18.4 pg/mL to 150 pg/mL)).

Means for Solving the Problems

The present inventors analyzed blood samples derived from patients whose BNP values were within the range between the above-mentioned thresholds and who were scheduled to undergo a cardiac catheterization test from the viewpoint of quality, and as a result have found that the value of the ratio between a detected levels of a specific BNP molecule selected from a BNP molecular group containing BNP molecules different in mass number and a detected levels of another specific BNP molecule is significantly different between the patients diagnosed with significant stenosis by a cardiac catheterization test and those not diagnosed with significant stenosis by a cardiac catheterization test, which has led to the completion of the present invention.

The present invention includes the following.

(1) A method for assessing myocardial ischemia comprising subjecting a blood sample which is derived from a test subject and which contains a B-type natriuretic hormone (BNP) molecular group containing at least two selected from the group consisting of BNP 1-32 molecule (SEQ ID No. 1), BNP 3-32 molecule (SEQ ID No. 2), BNP 4-32 molecule (SEQ ID No. 3), BNP 5-32 molecule (SEQ ID No. 4), and a molecule having a mass number larger than that of BNP 5-32 molecule by 16 Da to a detection process capable of distinguishing and quantifying the individual BNP molecules different in mass number to detect the BNP molecular group, wherein myocardial ischemia in the test subject is assessed using, as an index, a ratio between a detected intensity of at least one molecule selected from the BNP molecular group and a detected intensity of at least one other molecule selected from the BNP molecular group.

Assessing myocardial ischemia also means determining the presence or absence of coronary stenosis. More specifically, determining the presence or absence of ischemic heart disease and determining the presence or absence of restenosis after PCI are included.

In the present invention, the BNP 1-32 molecule refers to a mature Bb-type natriuretic hormone composed of 32 amino acids, and has an amino-acid sequence represented by SEQ ID No. 1 (or when a B-type natriuretic hormone precursor composed of 108 amino acids is expressed as BNP 1-108, BNP 77-108 corresponds to a mature B-type natriuretic hormone BNP 1-32 in the present invention).

The BNP 3-32 molecule refers to a fragment formed from BNP 1-32 molecule by processing of N-terminal two amino acids SP (represented by one-letter abbreviations of amino acids, the same goes for the following), and has an amino-acid sequence represented by SEQ ID No. 2. The BNP 4-32 molecule refers to a fragment formed from BNP 1-32 molecule by processing of N-terminal three amino acids SPK, and has an amino-acid sequence represented by SEQ ID No. 3. The BNP 5-32 molecule refers to a fragment formed from BNP 1-32 molecule by processing of N-terminal four amino acids SPKM (the first four amino acids of SEQ ID No. 1), and has an amino-acid sequence represented by SEQ ID No. 4.

In the present invention, the B-type natriuretic hormone (BNP) molecular group contains at least two selected from the group consisting of mature B-type natriuretic hormone molecule (i.e., BNP 1-32 molecule), BNP 3-32 molecule, BNP 4-32 molecule, BNP 5-32 molecule, and a molecule having a mass number larger than that of BNP 5-32 by 16 Da, and may further contain, in addition to these molecules, fragments formed from BNP 1-32 by processing and derivatives derived from them.

(2) The method according to the above (1), wherein the ratio between a detected intensity of at least one molecule selected from the molecular group and a detected intensity of at least one other molecule selected from the molecular group is a ratio between a sum of a detected intensity of the BNP 1-32 molecule and a detected intensity of the BNP 3-32 molecule, and a detected intensity of the BNP 5-32 molecule.

More specifically, the ratio described in the above (2) is a ratio represented by the following formula 1 or its inverse ratio:

{I(BNP 1-32)+I(BNP 3-32)}/I(BNP 5-32)　　　(formula 1)

wherein I(BNP 1-32) represents a detected intensity of the BNP 1-32 molecule, I(BNP 3-32) represents a detected intensity of the BNP 3-32 molecule, and I(BNP 5-32) represents a detected intensity of the BNP 5-32 molecule.

(3) The method according to the above (1) or (2), wherein the ratio between a detected intensity of at least one molecule selected from the molecular group and a detected intensity of at least one other molecule selected from the molecular group is a ratio between a detected intensity of the BNP 3-32 molecule and a detected intensity of the BNP 5-32 molecule.

More specifically, the ratio described in the above (3) is a ratio represented by the following formula 2 or its inverse ratio:

I(BNP 3-32)/I(BNP 5-32)　　　(formula 2)

wherein I(BNP 3-32) represents a detected intensity of the BNP 3-32 molecule and I(BNP 5-32) represents a detected intensity of the BNP 5-32 molecule.

In the above (2) and (3), the measured value of BNP of a blood specimen is preferably 18 pg/mL or higher or 21.9 pg/mL or higher.

In the above (2) and (3), the myocardial ischemia is preferably one caused by ischemic heart disease or by restenosis after PCI.

(4) The method according to any one of the above (1) to (3), wherein the ratio between a detected intensity of at least one molecule selected from the molecular group and a detected intensity of at least one other molecule selected from the molecular group is a ratio between a detected intensity of the molecule having a mass number larger than that of BNP 5-32 molecule by 16 Da and a detected intensity of the BNP 5-32 molecule.

More specifically, the ratio described in the above (4) is a ratio represented by the following formula 3 or its inverse ratio:

I(BNP 5-32+)/I(BNP 5-32)　　　(formula 3)

wherein I(BNP 5-32) represents a detected intensity of the BNP 5-32 molecule and I(BNP 5-32+) represents a detected intensity of the molecule having a mass number larger than that of BNP 5-32 molecule by 16 Da.

(5) The method according to any one of the above (1) to (4), wherein the blood sample is a blood specimen itself of a test subject having a measured value of BNP of 18 pg/mL to 150 pg/mL, or is prepared from the blood specimen.

(6) The method according to any one of the above (1) to (5), wherein the myocardial ischemia is one caused by ischemic heart disease or by restenosis after PCI.

In the above (1) to (6), the blood sample may be prepared from a blood specimen collected from the test subject with the use of a blood collection tube containing at least aprotinin.

In the above (1) to (6), the blood specimen is preferably a plasma specimen.

(7) The method according to any one of the above (1) to (6), wherein the blood sample is prepared by subjecting the blood specimen of the test subject to immunological enrichment using an antibody against the B-type natriuretic hormone molecular group.

In the above (1) to (7), the individual BNP molecules different in mass number may be distinguished and quantified by a method based on bio-specific affinity or by mass spectrometry.

Effects of the Invention

According to the present invention, it is possible to less-invasively assess a disease state caused by myocardial ischemia (e.g., ischemic heart disease or restenosis).

Further, according to the present invention, it is possible to determine the presence or absence of cardiovascular disease even from a blood sample having a BNP value from which the presence or absence of cardiovascular disease cannot be determined and only an ambiguous determination that there is suspicion of some kind of cardiovascular disease is made by a conventional method (i.e., a BNP value in the range between the thresholds (18.4 pg/mL to 150 pg/mL) for determining whether there is suspicion of heart failure).

The effects of the present invention will be described more specifically below.

The method according to the present invention uses not a conventional index based on the quantity of BNP (i.e., BNP value) but an index based on the quality of BNP. This makes it possible to obtain, from a blood sample, information that cannot be obtained only from the index based on the quantity of BNP. That is, the present invention makes it possible for the first time to assess myocardial ischemia only through a blood test.

As described above, since the method according to the present invention uses a novel index, it is possible to assess a cardiac disease state even from a blood sample having a BNP value in the range of 18.4 pg/mL to 150 pg/mL from which a cardiac disease state cannot be clearly assessed through a conventional blood test. Further, the effectiveness of the novel index used in the present invention is specific to ischemia, and therefore the presence or absence of myocardial ischemia also in a patient with a disease associated with a high BNP value (e.g., chronic heart failure) can be determined.

The method according to the present invention is applied to a blood test, and is therefore much easier and less invasive than a conventional invasive examination method (e.g., a cardiac catheterization test). Therefore, for the sake of higher accuracy, it is only necessary to perform an invasive test on only patients diagnosed as possibly having stenosis by a previously-performed blood test. This makes it possible to avoid an unnecessary cardiac catheterization test, thereby significantly reducing a burden on the body of a patient and test cost. A cardiac catheterization test is conventionally performed about every six months, and therefore even when restenosis requiring treatment occurs within six months, it is impossible to appropriately treat restenosis. However, the less-invasive blood test can be easily and repeatedly performed, and therefore restenosis can be appropriately treated earlier.

Thus, according to the method of the present invention, unlike a conventional examination method, ischemia can be reliably assessed and early detected only through an easy, less-invasive, and economic blood test. Eventually, the method according to the present invention can be applied to the assessment of arteriosclerosis. Further, as described above, the significance of BNP in a blood sample having a BNP value, from which a cardiac disease state cannot be accurately assessed through a conventional blood test, has become apparent, and therefore there is a possibility that BNP fragments and modified fragments thereof assist drug discovery.

Figure 10:
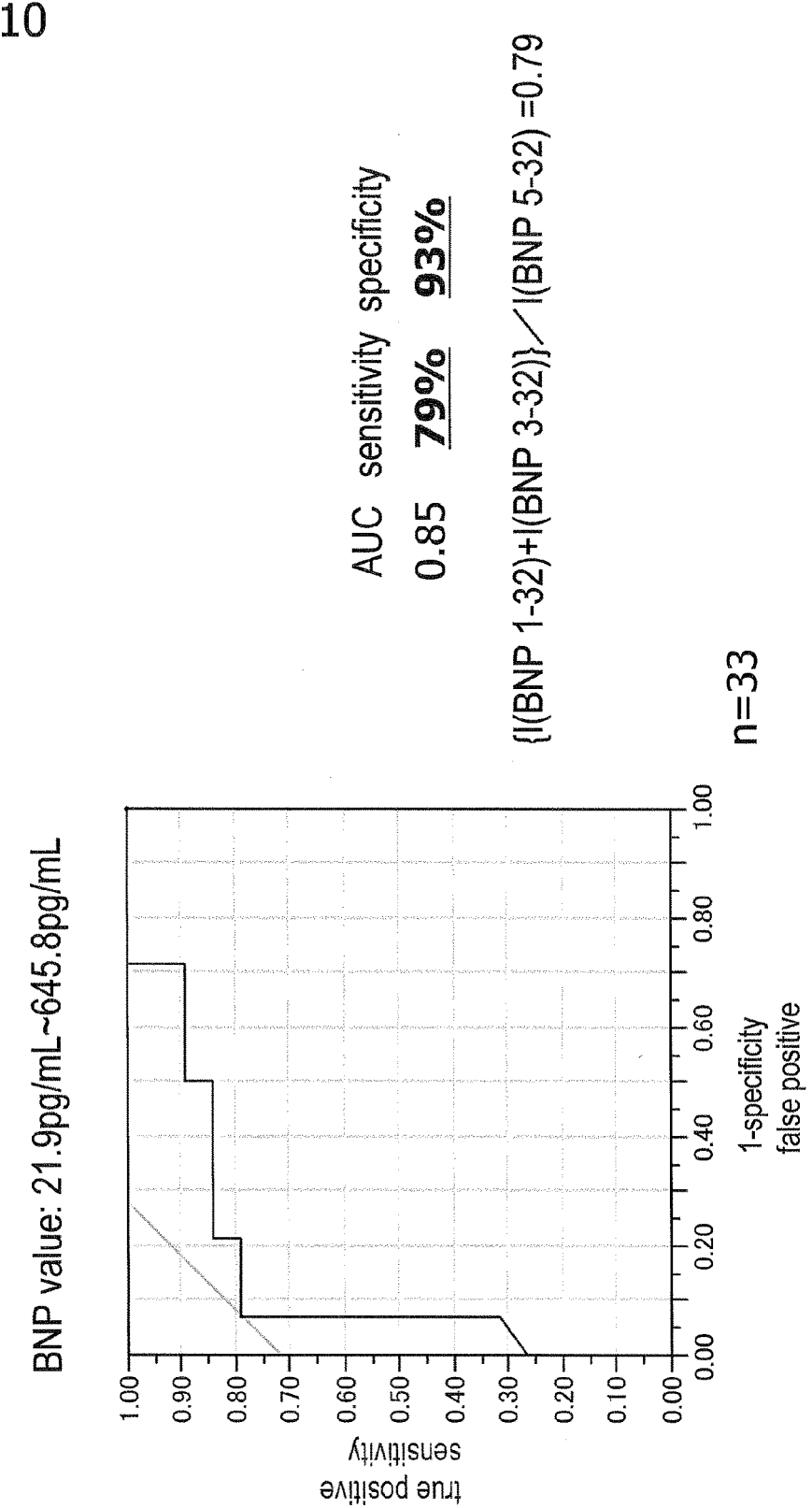

FIG. 10 is a graph obtained in Example 6, which shows the result of analyzing MS signal patterns and examining the correlation between the index of {I(BNP 1-32)+I(BNP 3-32)/I(BNP 5-32)} and the presence or absence of significant stenosis by ROC curve analysis.

Figure 11:
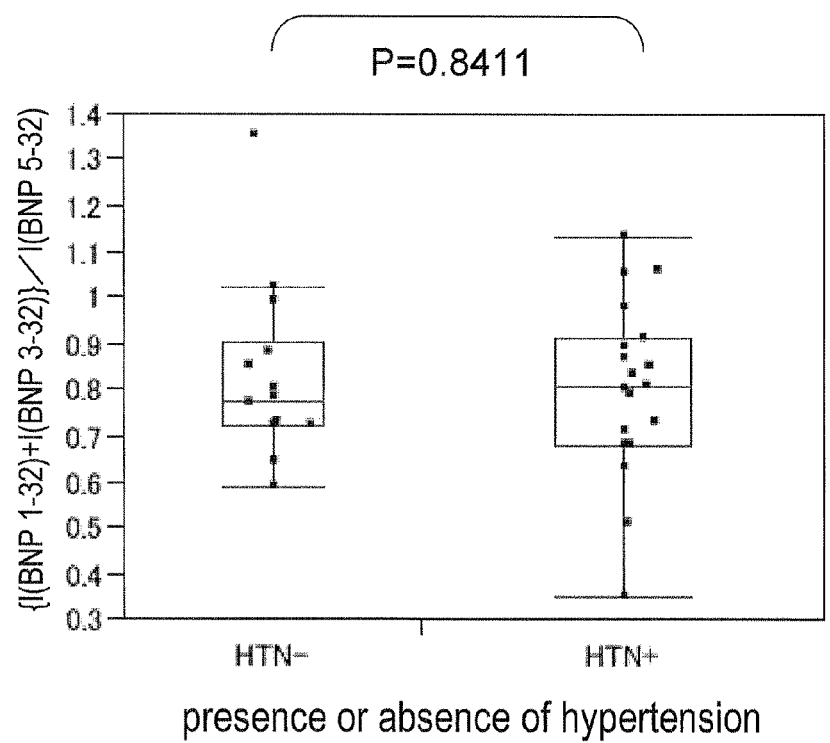

FIG. 11 is a graph obtained in Comparative Example 1, which shows the result of examining the correlation, regarding 33 clinical specimens whose BNP values were in the range of 21.9 pg/mL to 645.8 pg/mL, using an index of {I(BNP 1-32)+I(BNP 3-32)/I(BNP 5-32)}, between the index and the presence or absence of hypertension.

Figure 12:
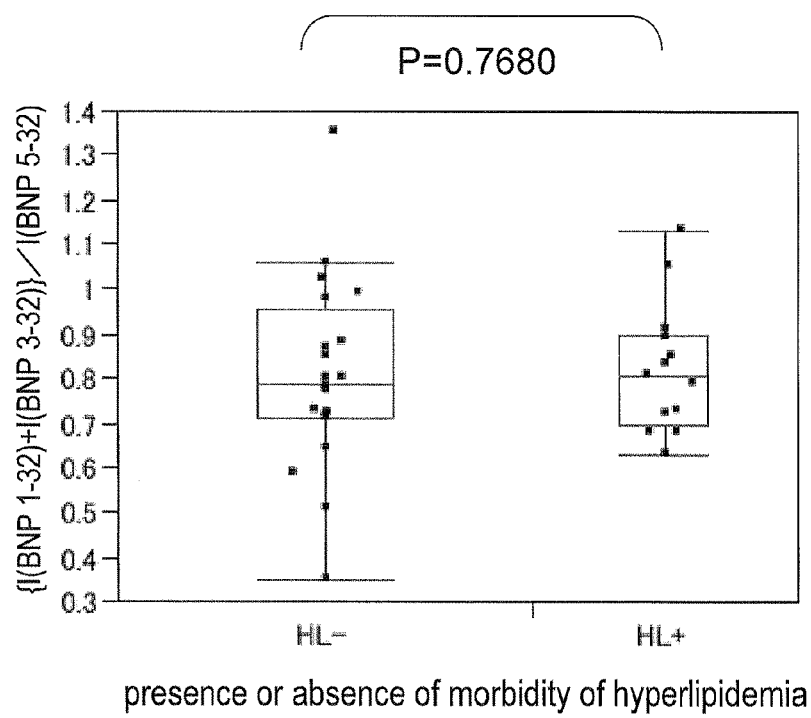

FIG. 12 is a graph obtained in Comparative Example 2, which shows the result of examining the correlation, regarding 33 clinical specimens whose BNP values were in the range of 21.9 pg/mL to 645.8 pg/mL, using an index of {I(BNP 1-32)+I(BNP 3-32)/I(BNP 5-32)}, between the index and the presence or absence of hyperlipidemia.

Figure 13:
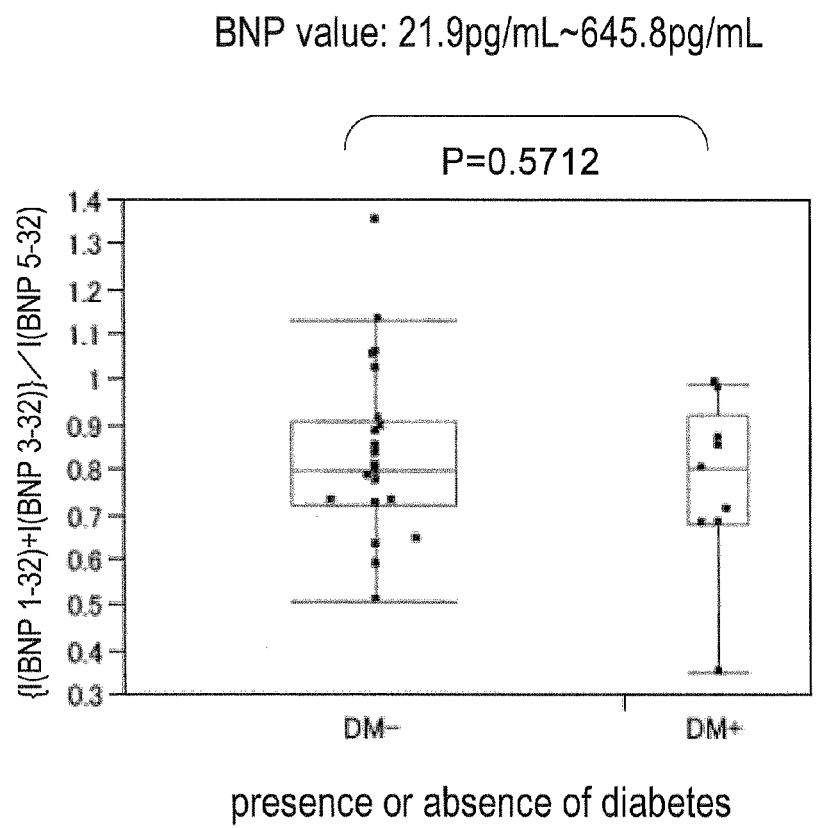

FIG. 13 is a graph obtained in Comparative Example 3, which shows the result of examining the correlation, regarding 33 clinical specimens whose BNP values were in the range of 21.9 pg/mL to 645.8 pg/mL, using an index of {I(BNP 1-32)+I(BNP 3-32)/I(BNP 5-32)}, between the index and the presence or absence of diabetes.

Figure 14:
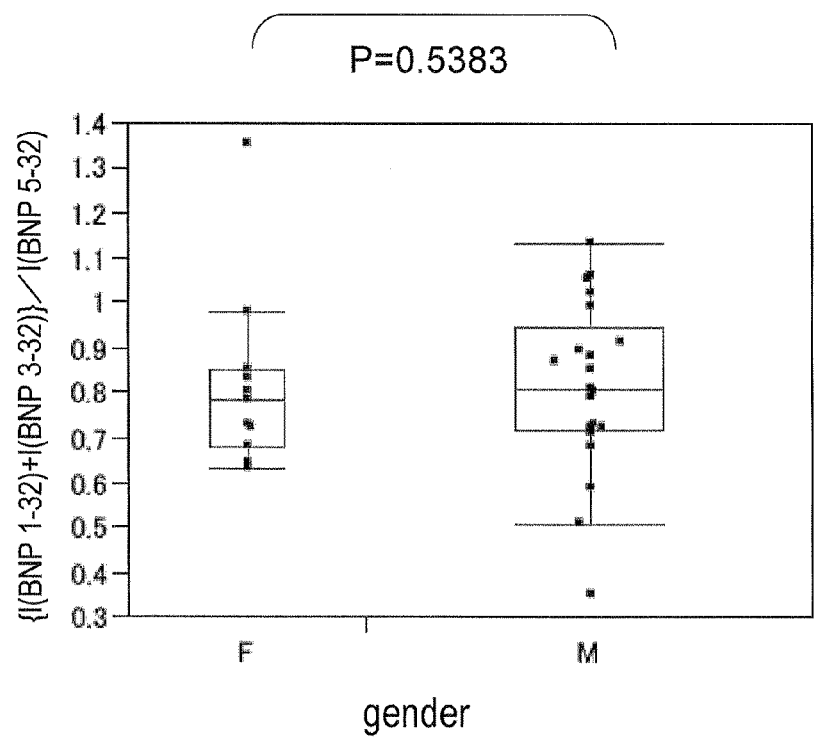

FIG. 14 is a graph obtained in Comparative Example 4, which shows the result of examining the correlation, regarding 33 clinical specimens whose BNP values were in the range of 21.9 pg/mL to 645.8 pg/mL, using an index of {I(BNP 1-32)+I(BNP 3-32)/I(BNP 5-32)}, between the index and gender.

Figure 15:
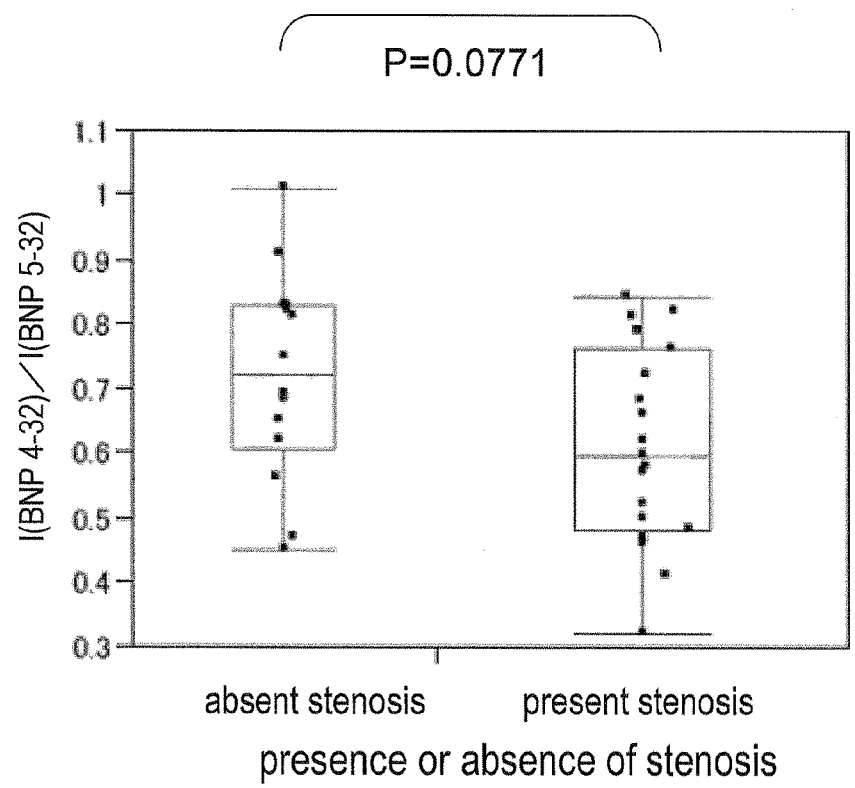

FIG. 15 is a graph obtained in Example 7, which shows the result of analyzing the MS signal patterns regarding 33 clinical specimens whose BNP values were in the range of 21.9 pg/mL to 645.8 pg/mL and examining the correlation, using an index of I(BNP 4-32)/I(BNP 5-32), between the index and the presence or absence of significant stenosis.

Figure 16:
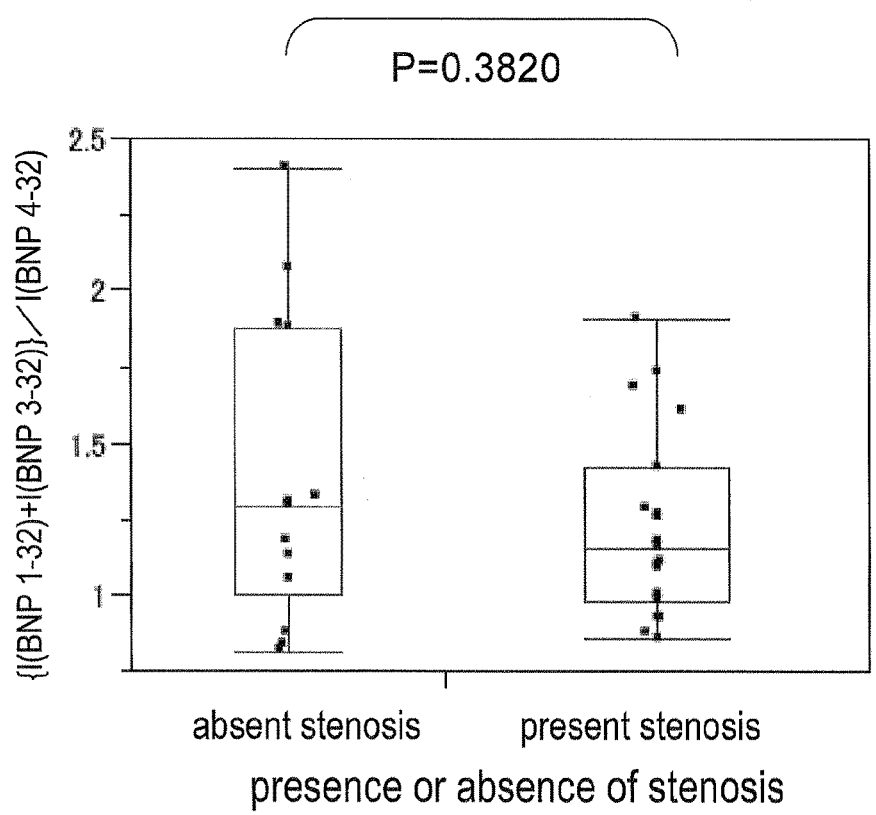

FIG. 16 is a graph obtained in Example 8, which shows the result of analyzing the MS signal patterns regarding 33 clinical specimens whose BNP values were in the range of 21.9 pg/mL to 645.8 pg/mL and examining the correlation, using an index of {I(BNP 1-32)+I(BNP 3-32)/I(BNP 4-32)}, between the index and the presence or absence of significant stenosis.

BEST MODE FOR CARRYING OUT THE INVENTION

1. Blood Specimen 1-1. Test Subject

Any person may become a test subject to be assessed by a method according to the present invention regardless of the presence or absence of a chief complaint. Specific examples of the test subject include patients who are undergoing a comprehensive medical examination, patients with ischemic heart disease, patients who underwent PCI, and patients with heart failure. Particularly, patients who are required to undergo a cardiac catheterization test in a conventional examination procedure may be mentioned. Further, the test subject may be a person with a disease such as hypertension, hyperlipidemia, or diabetes or a person suspected to have such a disease.

The present invention provides a method for assessing myocardial ischemia in a test subject. As used herein, "myocardial ischemia" refers to a state where oxygen is not sufficiently supplied to the heart due to coronary stenosis caused by, for example, arteriosclerotic changes. Therefore, the present invention may also be regarded as a method for determining the presence or absence of coronary stenosis in a test subject. In the present invention, a specific disease state caused by myocardial ischemia is not particularly limited, and examples thereof include ischemic heart disease and restenosis after PCI.

As specific examples of ischemic heart disease, cardiac angina and myocardial infarction may be usually mentioned. The present invention allows the diagnosis of myocardial ischemia that cannot be diagnosed through a conventional blood test, and is therefore useful in that it can be applied to the diagnosis of cardiac angina that cannot be diagnosed through a conventional blood test.

Particularly, the present invention is very useful in that it can be applied to the diagnosis of the presence or absence of restenosis, which may occur after PCI, as a stage prior to a cardiac catheterization test. Specific examples of PCI include stent placement, coronary angioplasty with balloon, cutting balloon catheter, and atherectomy.

It is to be noted that in the present invention, the presence of stenosis or of significant stenosis means that the degree of stenosis as determined by coronary angiography is 75% or higher (left main coronary trunk: 50% or higher).

1-2. Form of Blood Specimen

A blood specimen used in the present invention may be in the form of whole blood, plasma, or serum. Among them, a blood specimen in the form of plasma is preferably used. By using a blood specimen in the form of plasma, it is possible to prevent unnecessary fragmentation (e.g., C-terminal cleavage) of BNP to be detected in a detection process which will be described later, thereby making it possible to more accurately perform assessment.

1-3. Component that May be Added to Blood Specimen

A blood specimen may contain a blood stabilizing agent appropriately.

Examples of the blood stabilizing agent include protease inhibitors and anticoagulants. Specific examples of such blood stabilizing agents include aprotinin, ethylenediaminetetraacetic acid, heparin, citric acid, and sodium fluoride. The type of blood stabilizing agent to be used may be appropriately selected by those skilled in the art. In the present invention, at least aprotinin is particularly preferably used. More specifically, a blood collection tube to be used preferably contains aprotinin and EDTA. By using a blood collection tube containing aprotinin and EDTA, it is possible to prevent unnecessary fragmentation of BNP to be detected in a detection process which will be described later, thereby making it possible to more accurately perform assessment.

1-4. BNP Value of Blood Specimen

As used in the present invention, "measured value of BNP" or "BNP value" refers to an index widely clinically applied as a marker of heart failure or the like. The BNP value is measured by a well-known method such as an EIA (enzyme immunoassay) method. In the present invention, from the viewpoint of quality, the BNP value is the total concentration of a mixture of BNP molecules different in molecular weight including a BNP molecular group to be detected in a detection process which will be described later.

The present invention is useful for the diagnosis of ischemia. The BNP value of a blood specimen to be used in the present invention is not particularly limited, and a blood specimen having any BNP value may be used in the present invention.

For example, the present invention is useful even when a blood specimen has a BNP value in the range of 18 pg/mL to 150 pg/mL. Conventionally, when a BNP value as determined through a blood test is within the above range, the presence or absence of abnormalities is unclear, and therefore a BNP value within the above range is not regarded as important information for the diagnosis of heart failure. However, the method according to the present invention is capable, even when the BNP value of a blood specimen is within the above range, of determining the presence or absence of abnormalities by utilizing the fact that the value of an index which will be described later is significantly different between the presence and absence of coronary stenosis.

Preferred examples of such an index used for a blood specimen having a BNP value within the above range include indices which will be described later in 4-1-1, 4-1-2, and 4-1-3.

When a blood specimen has a BNP value within the above range, there is a case where determination of the presence or absence of abnormalities can be more reliably made when the blood specimen has a BNP value in the range of 20 pg/mL to 150 pg/mL, 30 pg/mL to 150 pg/mL, or 40 pg/mL to 150 pg/mL than when the blood specimen has a BNP value in the range of 18 pg/mL to 150 pg/mL. An example of an index showing such a tendency includes an index which will be described later in 4-1-3.

Further, the present invention is useful also when the BNP value of a blood specimen exceeds 150 pg/mL. Conventionally, when a BNP value as determined by a blood test is within the above range, a diagnosis of "suspected heart failure" can only be made. However, the method according to the present invention is capable, also when a patient has a BNP value within the above range and is strongly suspected of having heart failure, of determining the presence or absence of coronary stenosis. It is to be noted that the upper limit of a BNP value within the above range is not particularly limited, and may be any clinically possible value exceeding 150 pg/mL. For example, a BNP value of about 650 pg/mL is clinically possible, but a BNP value exceeding 650 pg/mL is, of course, clinically possible.

As has been described above, the present invention is useful not only when the BNP value of a blood specimen is in the range of 18 pg/mL to 150 pg/mL but also when the BNP value of a blood specimen exceeds 150 pg/mL. That is, the present invention is useful when the BNP value of a blood specimen is 18 pg/mL or higher. In this case, the BNP value of a blood specimen is preferably 20 pg/mL or higher.

Preferred examples of an index used for a blood specimen having such a BNP value include indices which will be described later in 4-1-1 and 4-1-2.

On the other hand, the present invention can be used also when the BNP value of a blood specimen is less than 18 pg/mL. Conventionally, when a BNP value as determined through a blood test is within the above range, a diagnosis of "nothing abnormal detected" is made. However, more detailed analysis can be made by the method according to the present invention from the viewpoint of quality. When about 500 μL of a specimen is used to detect BNP by, for example, mass spectrometry, there is a case where the amount of BNP is less than the limit of detection. However, such analysis can be made by appropriately increasing the amount of a specimen used (e.g., by increasing the amount of a specimen to 1 mL or 2 mL).

2. Blood Sample

As used in the present invention, "blood sample" refers to a sample to be subjected to a detection process. Therefore, a blood sample may be prepared by appropriately treating the above-mentioned blood specimen, or the above-mentioned blood specimen may be used directly as a blood sample.

2-1. Molecules Contained in Blood Sample as Detection Targets

Molecules to be detected in the present invention are molecules constituting a B-type natriuretic hormone (BNP) molecular group present in a blood sample. The molecules constituting a BNP molecular group may include BNP 1-32, fragments formed from BNP 1-32 by processing, and/or derivatives derived from them. These molecules constituting a BNP molecular group have to include molecules generated in the body of a test subject.

The molecules constituting a BNP molecular group may include molecules formed by a change (e.g., processing or a chemical change that never occurs in a living body) of molecules generated in the body of a test subject during blood collection or sample preparation, but a blood sample is preferably prepared so as to contain such molecules as little as possible. For example, a blood sample is preferably prepared by using a blood specimen in the form of plasma or by using a blood collection tube containing aprotinin and EDTA. This makes it possible to suppress cleavage at the C-terminal of BNP or nonspecific cleavage at the N-terminal of BNP.

More specifically, BNP 1-32 is a mature B-type natriuretic hormone composed of 32 amino acids, and has an amino-acid sequence represented by SEQ ID No. 1. When a B-type natriuretic hormone precursor composed of 108 amino acids is expressed as BNP 1-108, BNP 77-108 corresponds to a mature B-type natriuretic hormone BNP 1-32 in the present invention.

As fragments formed from BNP by processing, at least BNP 3-32 molecule, BNP 4-32 molecule, and BNP 5-32 molecule may be mentioned from the viewpoint of more accurately reflecting conditions inside the body of a test subject. The BNP 3-32 molecule is a fragment formed from BNP 1-32 molecule by processing of N-terminal two amino acids SP (represented by one letter abbreviations of amino acids, the same goes for the following), and has an amino-acid sequence represented by SEQ ID No. 2. The BNP 4-32 molecule is a fragment formed from BNP 1-32 molecule by processing of N-terminal three amino acids SPK, and has an amino-acid sequence represented by SEQ ID No. 3. The BNP 5-32 molecule is a fragment formed from BNP 1-32 molecule by processing of N-terminal four amino acids SPKM (the first four amino acids of SEQ ID No. 1), and has an amino-acid sequence represented by SEQ ID No. 4.

Specific examples of derivatives derived from BNP 1-32 or from fragments formed from BNP 1-32 by processing include derivatives formed by a chemical change of their original molecules. More specifically, the chemical change is, for example, oxidation. Mainly, methionine may undergo oxidation.

A BNP molecular group in the present invention contains, as its one of constituent molecules, a molecule having a mass number larger than that of BNP 5-32 by 16 Da. It has been confirmed by the present inventors that a difference in mass number between this molecule and BNP 5-32 is 16 Da, and, as will be described later, this molecule can be immunologically enriched together with other BNP fragments by one antibody, and this molecule disappears by the action of a deoxidizer. Therefore, it may be considered that this molecule is an oxide of BNP 5-32. In the present invention, this molecule is not identified in terms of structure, and is expressed as "molecule having a mass number larger than that of BNP 5-32 by 16 Da" in terms of only mass number. For the sake of simplicity, this molecule is included in the above-mentioned "derivatives".

That is, a BNP molecular group to be detected in the present invention contains at least two selected from the group consisting of BNP 1-32 molecule, BNP 3-32 molecule, BNP 4-32 molecule, BNP 5-32 molecule, and a molecule having a mass number larger than that of BNP 5-32 by 16 Da, and may further contain, in addition to these molecules, fragments formed from BNP 1-32 by processing and derivatives derived from them.

2-2. Immunological Enrichment

In the present invention, a BNP molecular group contained in a blood specimen is preferably immunologically enriched. An immunological enrichment method to be used in the present invention is not particularly limited as long as a BNP molecular group contained in a blood sample can be specifically enriched by bringing the BNP molecular group into contact with an antibody against the BNP molecular group under conditions where immune complexes can be formed. Such an immunological enrichment method may be appropriately selected by those skilled in the art. In addition, a specific protocol may also be easily selected by those skilled in the art.

Specific examples of such an immunological enrichment method include an immunoprecipitation method and affinity column chromatography. These methods are well-known to those skilled in the art, and their protocols are appropriately determined by those skilled in the art.

In the present invention, an immunoprecipitation method is preferably used. According to this method, an immunoprecipitate is obtained by allowing a blood sample, an antibody against a target BNP molecular group, and a carrier for precipitation to coexist under conditions where immune complexes can be formed. This method is advantageous because of its simple operation, high cost performance, and very high versatility.

Examples of an antibody for use in immunological enrichment include antibodies capable of simultaneously recognizing BNP contained in a BNP molecular group to be enriched. Such an antibody may be appropriately prepared by those skilled in the art by using a region common to BNP molecules contained in a BNP molecular group to be enriched as an antibody capable of recognizing peptide fragments having such a common region.

Other examples of an antibody for use in immunological enrichment include mixtures of two or more kinds of antibodies recognizing individual BNP molecules contained in a BNP molecular group to be enriched, respectively. Such an antibody may be appropriately prepared by those skilled in the art by using a characteristic region of a specific BNP molecule contained in a BNP molecular group to be enriched as an antibody capable of recognizing peptide fragments having such a region.

A specific example of such an antibody includes KYBNPII (manufactured by Shionogi & Co., Ltd.). KYBNPII can simultaneously recognize at least BNP 1-32 molecule, BNP 3-32 molecule, BNP 4-32 molecule, BNP 5-32 molecule, and a molecule having a mass number larger than that of BNP 5-32 by 16 Da.

3. Detection Process

The above-mentioned blood sample is subjected to a detection process. The detection process is performed using a method capable of distinguishing and quantifying BNP molecules different in mass number, that is, a method capable of distinguishing and quantifying individual molecules contained in a BNP molecular group. As used herein, "quantifying" does not refer to measuring absolute amounts of individual BNP molecules, and it is only necessary to measure relative amounts of individual BNP molecules. A method to be used in the detection process is not particularly limited as long as it is such a method as described above, and may be appropriately selected by those skilled in the art. Specific examples of such a method include a method based on bio-specific affinity and mass spectrometry.

3-1. Method Based on Bio-Specific Affinity

In a case where a method based on bio-specific affinity is used, a blood sample to be subjected to the detection process may be obtained by subjecting a blood specimen to the above-mentioned immunological enrichment, or a blood specimen (e.g., a plasma specimen) may be used directly as a blood sample to be subjected to the detection process without being subjected to the above-mentioned immunological enrichment.

A method based on bio-specific affinity is well-known to those skilled in the art, and is not particularly limited as long as it is carried out by bringing a blood sample into contact with substances having bio-specific affinity under conditions where complexes can be formed by bio-specific affinity to measure the levels of the resulting signals. Such a method based on bio-specific affinity may be appropriately selected by those skilled in the art. In addition, a specific protocol may also be easily selected by those skilled in the art.

More specifically, the method is preferably immunoassay. In this case, a blood sample is brought into contact with antibodies under conditions where immune complexes can be formed to measure the levels of the resulting signals. Specific examples of such immunoassay include immunoassays including competitive and non-competitive assay systems such as Western blotting, radioimmunoassay, ELISA, sandwich immunoassay, immunoprecipitation, precipitation reaction, gel diffusion precipitin reaction, immunodiffusion, aggregation measurement, complement fixation assay, immunoradiometric assay, fluorescence immunoassay, and protein A immunoassay. A more specific protocol may be easily selected by those skilled in the art.

The above-mentioned immunoassay uses two or more kinds of antibodies recognizing individual BNP molecules contained in a BNP molecular group, respectively. Such an antibody may be appropriately prepared by those skilled in the art by using a characteristic region of a specific BNP molecule contained in a BNP molecular group to be enriched as an antibody capable of recognizing peptide fragments having such a region.

3-2. Mass Spectrometry

In a case where mass spectrometry is used, a blood sample to be subjected to the detection process is preferably obtained by subjecting a blood specimen to the above-mentioned immunological enrichment.

Mass spectrometry is well-known to those skilled in the art, and an ionization means and a detection means which allow detection of protein and/or peptide molecules are not particularly limited, and may be appropriately selected by those skilled in the art. Examples of an ionization method to be used include electron ionization (EI), chemical ionization (CI), fast atom bombardment (FAB), electrospray ionization (ESI), atmospheric pressure chemical ionization (APCI), matrix-assisted laser desorption ionization (MALDI), and surface-enhanced laser desorption ionization (SELDI). Preferably, a MALDI-TOF mass spectrometer is used. In the case of SELDI, an antibody used in the above-mentioned immunological enrichment may be used.

4. Assessment Process

4-1. Index

In the present invention, the ratio between a detected intensity of at least one molecule selected from a BNP molecular group detected by the above-mentioned method and a detected intensity of at least one other molecule selected from the BNP molecular group is used as an index for assessment. This index is based on the quality of BNP, and is therefore different from a conventional index based on the quantity of BNP (i.e., BNP value). Therefore, unlike a conventional method, the index used in the present invention makes it possible to obtain, from a blood sample, information that cannot be obtained only from an index based on the quantity of BNP. More specifically, the index used in the present invention makes it possible to determine the presence or absence of myocardial ischemia, that is, the presence or absence of significant coronary stenosis (more specifically, significant coronary stenosis having a degree of stenosis of 75% or higher (left main coronary trunk: 50% or higher) as determined by coronary angiography) from a blood sample.

4-1-1. Index Example 1

As one example of the index used in the present invention, the ratio between the sum of a detected intensity of BNP 1-32 molecule and a detected intensity of BNP 3-32 molecule, and a detected intensity of BNP 5-32 molecule may be mentioned. More specifically, a ratio represented by the following formula 1 and its inverse ratio may be mentioned:

$$\{I(BNP\ 1\text{-}32) + I(BNP\ 3\text{-}32)\}/I(BNP\ 5\text{-}32) \quad \text{formula 1}$$

wherein (BNP 1-32) represents a detected intensity of BNP 1-32 molecule, I(BNP 3-32) represents a detected intensity of BNP 3-32 molecule, and I(BNP 5-32) represents a detected intensity of BNP 5-32 molecule.

The values of the ratio represented by the formula are significantly lower in a group of patients with stenosis than in a group of patients without stenosis. This tendency is higher when the BNP value of a specimen is, for example, 18 pg/mL or higher or 21.9 pg/mL or higher.

4-1-2. Index Example 2

It has been confirmed by the present inventors that BNP 1-32 molecule is easily decomposed and is therefore rapidly changed to BNP 3-32 after blood collection. Therefore, there is a case where almost no or no BNP 1-32 molecule is detected depending on the conditions of a clinical specimen etc. In this case, an index that ignores BNP 1-32 molecule taken into consideration in the case of the above-mentioned index example 1 may be used.

That is, as another example of the index used in the present invention, the ratio between a detected intensity of BNP 3-32 molecule and a detected intensity of BNP 5-32 molecule may be mentioned. More specifically, a ratio represented by the following formula 2 and its inverse ratio can be mentioned:

$$I(BNP\ 3\text{-}32)/I(BNP\ 5\text{-}32) \quad \text{(formula 2)}$$

wherein I(BNP 3-32) represents a detected intensity of BNP 3-32 molecule and I(BNP 5-32) represents a detected intensity of BNP 5-32 molecule.

The values of the ratio represented by the formula are significantly lower in a group of patients with stenosis than in a group of patients without stenosis. This tendency is higher when the BNP value of a specimen is, for example, 18 pg/mL or higher or 21 pg/mL or higher. Particularly, this tendency is high when no signal derived from BNP 1-32 molecule in a blood specimen is detected or when the intensity of the signal is negligibly low.

4-1-3. Index Example 3

As another example of the index used in the present invention, the ratio between a detected intensity of a molecule having a mass number larger than that of BNP 5-32 molecule by 16 Da and a detected intensity of BNP 5-32 molecule may be mentioned. More specifically, a ratio represented by the following formula 3 and its inverse ratio may be mentioned:

$$I(BNP\ 5\text{-}32+)/I(BNP\ 5\text{-}32) \quad \text{(formula 3)}$$

wherein I(BNP 5-32) represents a detected intensity of BNP 5-32 molecule and I(BNP 5-32+) represents a detected intensity of a molecule having a mass number larger than that of BNP 5-32 molecule by 16 Da.

The values of the ratio represented by the formula 3 are significantly higher in a group of patients with stenosis than in a group of patients without stenosis. This tendency is higher when the BNP value of a specimen is, for example, in the range of 18 pg/mL to 150 pg/mL, and is much higher when the BNP value of a specimen is in the range of 21 pg/mL to 150 pg/mL, 30 pg/mL to 150 pg/mL, or 40 pg/mL to 150 pg/mL.

4-2. Assessment Means

In a case where the presence or absence of stenosis is determined using such an index as described above, the above-mentioned ratio of a blood sample derived from a patient is preferably compared to a previously-determined reference value. The reference value may be set by, for example, determining in advance the values of the above-mentioned ratio of a plurality of test subjects and then analyzing, by a statistical analytical method, the results of a cardiac catheterization test performed on the test subjects to determine the presence or absence of stenosis.

An example of the statistical analytical method includes analysis using a Receiver-operating characteristic (ROC) curve. In a case where analysis using a ROC curve is used as the statistical analytical method, a value that minimizes the difference between sensitivity and specificity for distinguishing a stenosis group may be set as a reference value. The reference value may be appropriately adjusted to its optimum value by those skilled in the art according to individual requirements or circumstances of a clinical site such as prediction accuracy and preventive effect.

Further, the method according to the present invention may be used in combination with any other method. For example, the combined use of the method according to the present invention and another cardiovascular disease assessment method makes it possible to achieve a more highly reliable assessment.

EXAMPLES

The present invention will be described more specifically with reference to the following examples, but is not limited to the following examples. It is to be noted that, in mass spectrometric analysis, each of two samples simultaneously prepared from the same clinical specimen was analyzed twice by MS. The resulting total of four analytical data were analyzed, and only the result with a CV value of 15% or less was used.

Experimental Example 1

Study of Blood Collection Tube Etc

1) Plasma Preparation

Test subject: Blood was collected from a healthy person from whom informed consent had been obtained.

Blood collection: Blood was collected from the cubital vein of a test subject by a usual method. A study of a blood collection tube was made using an EDTA-aprotinin blood collection tube and an EDTA blood collection tube. In the case of serum preparation, a general blood collection tube containing a serum separating agent was used.

Treatment after blood collection: Just after blood collection, blood was externally spiked with BNP 1-32 (final concentration: 200 fmol/mL) and plasma separation was immediately performed (actual time spent on preparation was 15 to 30 minutes). Based on the result of study of changes with time, plasma separation was performed within 6 hours after the start of storage at 4° C. or on ice when it could not be performed just after blood collection. The thus obtained plasma was immediately frozen with liquid nitrogen and stored at −80° C.

The plasma sample was thawed and subjected to BNP enrichment which will be described later in detail in Experimental Example 2, and the resulting enriched BNP was analyzed by mass spectrometry.

Figure 1:
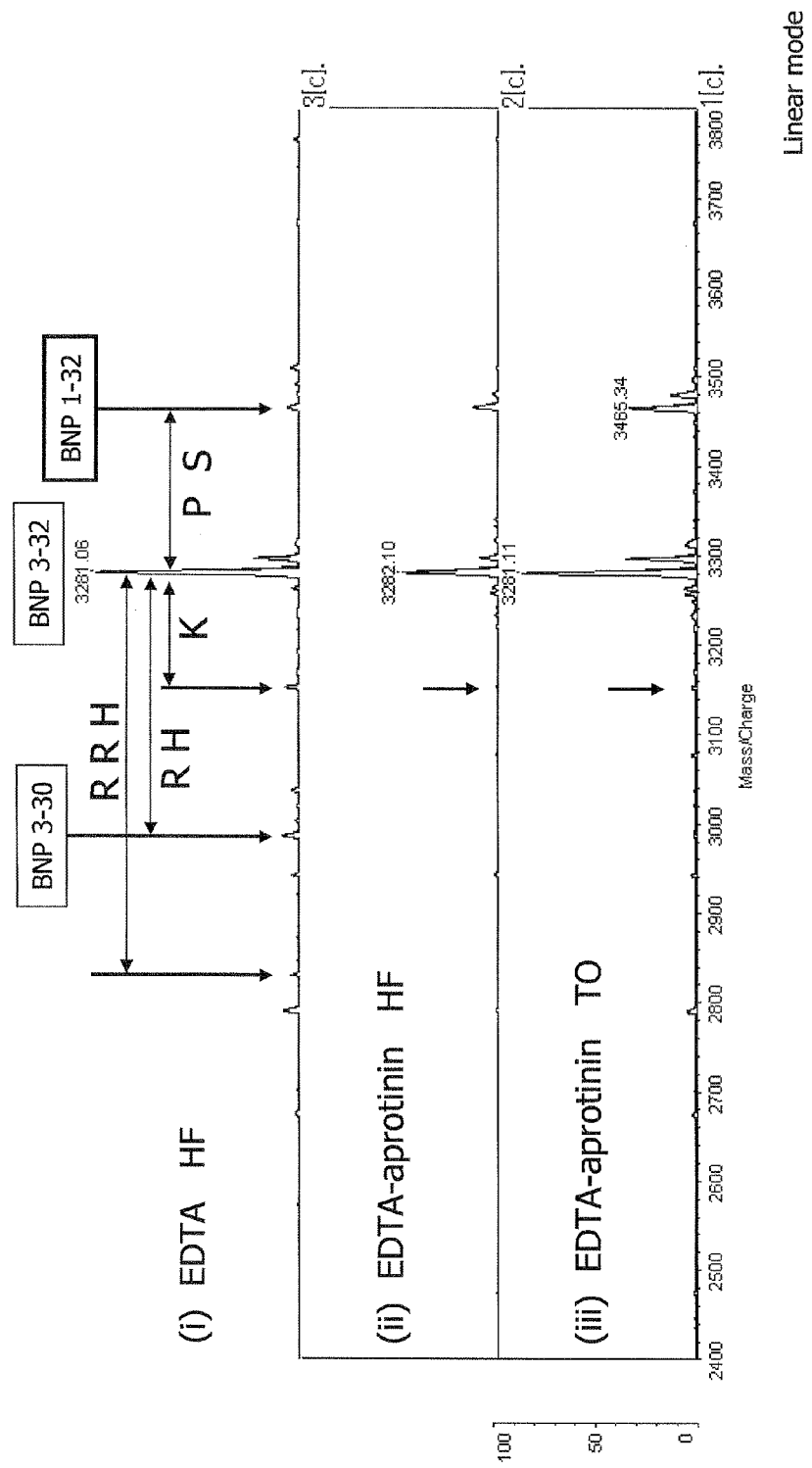
FIG. 1 shows MS spectra obtained in Experimental Example 1, which indicate that there is a difference in the processing of BNP between when blood is collected using an EDTA blood collection tube and when blood is collected using an EDTA-aprotinin blood collection tube.

The analytical results are shown in FIG. 1. As can be seen from FIGS. 1(i) to 1(iii), in each case, fragments (BNP 3-32) were formed by processing of N-terminal two amino acids SP (represented by one-letter abbreviations of amino acids, the same goes for the following). As conventionally reported, processing of N-terminal two amino acids SP occurred.

However, as shown in FIG. 1(i), in the case of using an EDTA blood collection tube, fragments formed by processing of N-terminal amino acids SPK and fragments formed by processing of C-terminal two amino acids RH or three amino acids RRH were also detected. Further, it has been confirmed that cleavage at the C-terminal region of BNP 1-32 is more likely to occur as time on ice increases (it has been also confirmed that cleavage the N-terminal of BNP 1-32 is more likely to occur as time on ice increases; these data are not shown).

On the other hand, as shown in FIGS. 1(ii) and 1(iii), in the case of using an EDTA-aprotinin blood collection tube, fragments formed by processing of N-terminal amino acids SPK were detected in trace amounts, but few fragments formed by processing of the C-terminal part of BNP 1-32 were detected.

As a result, it has been confirmed that in the case of using an EDTA blood collection tube, cleavage at the N-terminal or C-terminal region of BNP 1-32 is likely to occur, but in the case of using an EDTA-aprotinin blood collection tube, cleavage at the C-terminal region of BNP 1-32 is suppressed. That is, it can be considered that the state of BNP when present in a living body is more accurately reflected when an EDTA-aprotinin blood collection tube is used than when an EDTA blood collection tube is used.

It is to be noted that a study of changes with time between blood collection and plasma preparation was also made. More specifically, a plasma specimen obtained by performing plasma separation just after blood collection and a plasma specimen obtained by performing plasma separation after storage at 4° C. for 6 hours were analyzed, and as a result, it has been confirmed that there is no change between these specimens (data are not shown).

On the other hand, an experiment was performed in the same manner as described above except that serum separation was performed instead of plasma separation. As a result, it has been confirmed that the cleavage of BNP 1-32 immediately occurs at both the N-terminal and C-terminal regions in a serum (data are not shown).

Experimental Example 2

Determination of Specificity of Antibody

1) Plasma Preparation

Test subject: Blood was collected from a healthy person from whom informed consent had been obtained.

Blood collection: Blood was collected from the cubital vein of a test subject with the use of an EDTA-aprotinin blood collection tube.

Treatment after blood collection: Blood was stored on ice or at 4° C. just after blood collection. Plasma separation was performed within 6 hours after blood collection, and the resulting plasma was immediately frozen with liquid nitrogen and stored at −80° C. Then, the plasma was thawed, and Mixed BNP comprising BNP 1-32, BNP 3-32, BNP 4-32, and BNP 5-32 (each 5 fmol) was added thereto to prepare two BNP-added specimens (500 µL).

Further, two BNP-nonadded specimens (500 µL) were also prepared by plasma separation without addition of Mixed BNP. The thus obtained two BNP-nonadded specimens were frozen for preservation in the same manner as described above.

2) BNP Enrichment

BNP in the plasma was immunoprecipitated using KYB-NPII (supplied from Shionogi & Co., Ltd.) as a primary antibody and anti-mouse IgG-coupled beads ("Dynabeads M-280 Sheep anti-Rabbit IgG" manufactured by VERITAS Corporation, Catalog No. 112.03) as a secondary antibody.

More specifically, one of the above-mentioned BNP-added specimens and one of the above-mentioned BNP-nonadded specimens were each subjected to immunoprecipitation in the following manner.

20 µL of anti-mouse IgG-coupled beads were washed with PBS three times.

Then, 2 µL of KYBNPII was added to the beads, and the resulting mixture was incubated at room temperature for 1 hour to couple the KYBNPII to the beads.

As a control, anti-mouse IgG-coupled beads were incubated at room temperature for 1 hour without adding KYB-NPII.

These beads were washed with PBS five times, and then the KYBNPII-coupled beads were suspended in 20 W, of PBS, and the resulting suspension was placed on ice.

The specimen stored at −80° C. was quickly thawed in a warm bath of 37° C. and then placed on ice.

The thawed specimen (500 µl) was mixed with 50 µL, of PBS (×10), 440 µL of DDW, and 10% (w/v) Zwittergent (Calbiochem) so that the final volume of the specimen was 1 mL.

Then, 20 µL of the above-mentioned KYBNPII-coupled beads were added.

As a control, 20 µL of the above-mentioned beads incubated for 1 hour without adding KYBNPII were added.

The mixture of the specimen and the beads was incubated at room temperature for 1 hour to couple BNP in the plasma to the beads.

Then, the beads were washed with PBS four times.

Then, the beads were further washed with 20 mM $NH_4HCO_3$ once.

The elution of BNP from the beads was performed using 5 µL of 0.5% (v/v) TFA.

3) Mass Spectrometry of Enriched BNP

The following specimens (a) to (d) were analyzed by mass spectrometry.

(a): BNP-added specimen subjected to BNP enrichment (b): BNP-added specimen not subjected to BNP enrichment (c): BNP-nonadded specimen subjected to BNP enrichment (d): BNP-nonadded specimen not subjected to BNP enrichment In the case of the specimens (a) and (c) subjected to BNP enrichment, the total volume of eluate from the beads was dropped onto a MALDI target plate. On the other hand, also in the case of the specimens (b) and (d) not subjected to BNP enrichment, the total volume of eluate from the beads was dropped onto a MALDI target plate.

As a matrix, a mixture of 5 mg/mL DHB and 2.5 mg/mL CHCA was used.

After air drying, MS analysis was immediately performed using AXIMA-CFR plus.

The analysis was performed in linear mode. Calibration of m/z was performed using ACTH (18-39) fragment and Insulin oxidized B-chain.

Figure 2:
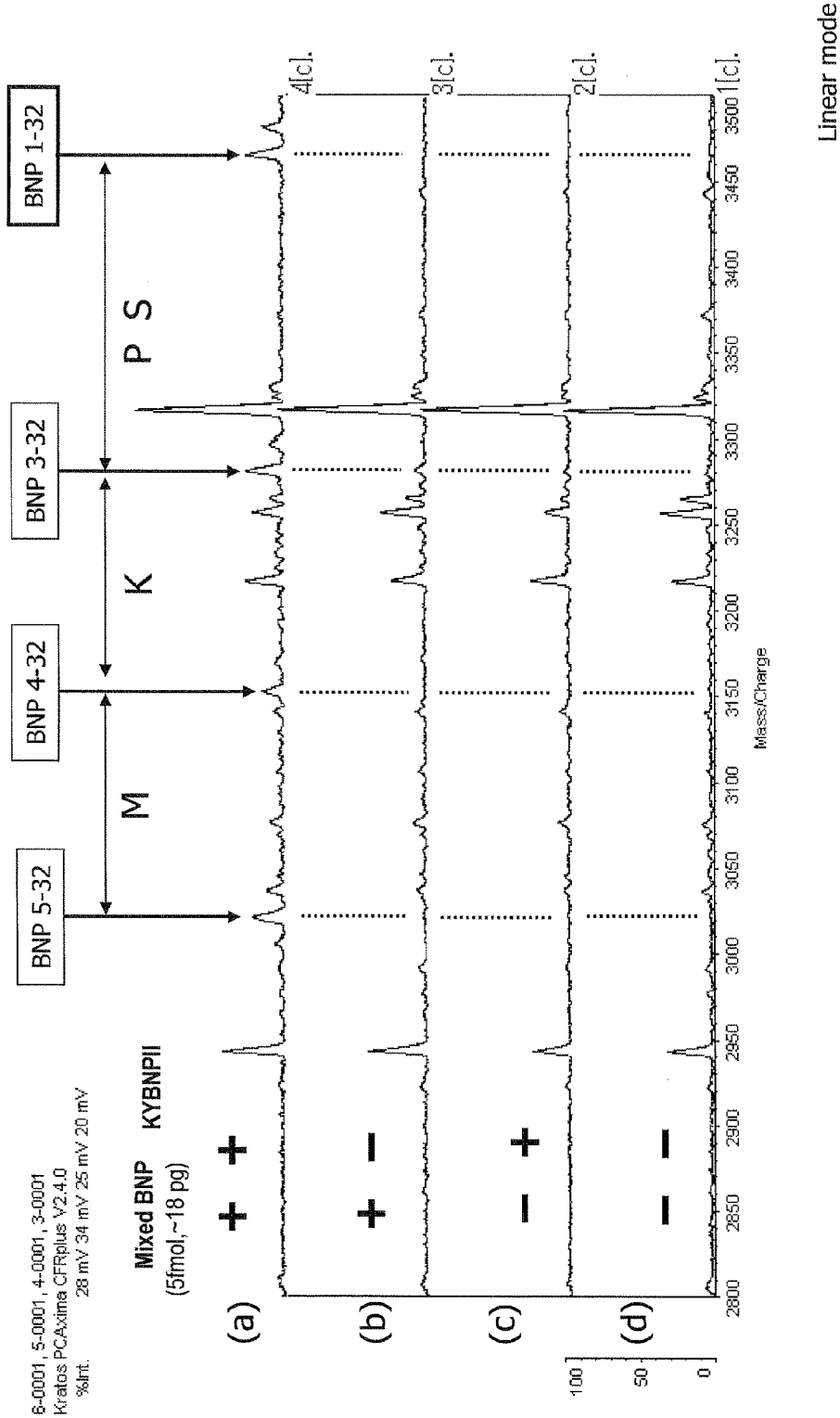
FIG. 2 shows MS spectra obtained in Experimental Example 2, which indicate that KYBNPII is an antibody that specifically recognizes BNP 1-32, BNP 3-32, BNP 4-32, and BNP 5-32.

The results of mass spectrometry of the specimens (a), (b), (c) and (d) are shown in FIG. 2. As shown in FIG. 2, only in the case of the BNP-added specimen (a) subjected to BNP enrichment, specific signals derived from BNP 1-32, BNP 3-32, BNP 4-32, and BNP 5-32 were obtained. From the result, it has been confirmed that the KYBNPII antibody is an antibody that specifically recognizes BNP 1-32, BNP 3-32, BNP 4-32, and BNP 5-32.

Experimental Example 3

Study of Limit of Detection (LOD)

Serum samples (e), (f), (g), (h), (i), and (j) were prepared by adding BNP 1-32 at the following concentration to 0.5 mL of commercially-available human serum. These serum samples (e) to (j) were subjected to BNP enrichment and mass spectrometry in the same manner as in Experimental Example 2.

Figure 3:
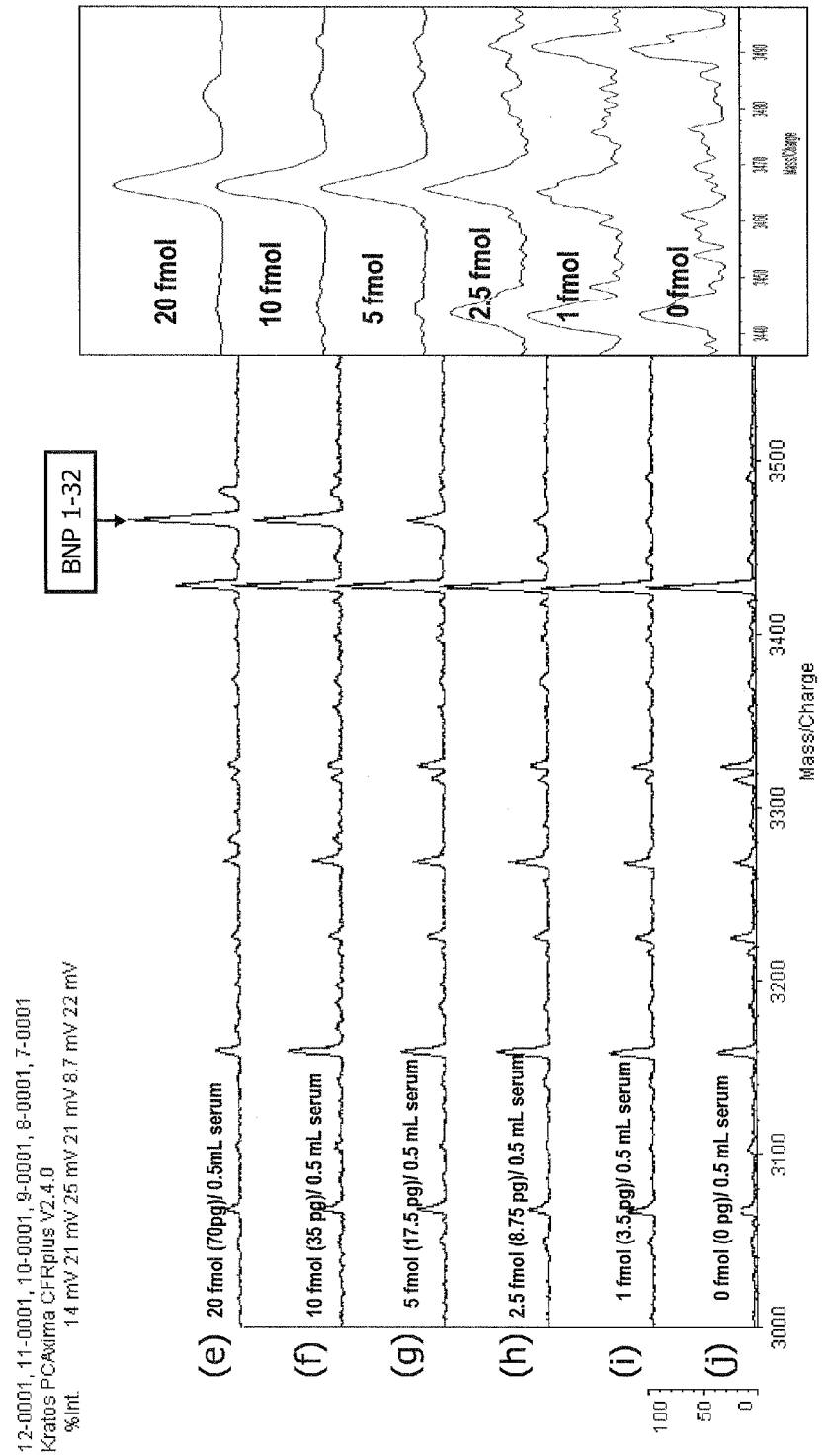
FIG. 3 shows MS spectra obtained in Experimental Example 3 in which the limit of detection of a method according to the present invention is examined.

(e): 20 fmol (70 pg)/0.5 mL serum (f): 10 fmol (35 pg)/0.5 mL serum (g): 5 fmol (17.5 pg)/0.5 mL serum (h): 2.5 fmol (8.75 pg)/0.5 mL serum (i): 1 fmol (3.5 pg)/0.5 mL serum (j): 0 fmol (0 pg)/0.5 mL serum The resulting MS spectra are shown in FIG. 3. As shown in FIG. 3, BNP contained in the sample (i) (1 fmol (3.5 pg)/0.5 mL serum) could be detected. From the result, the limit of detection is 2 fmol (7 pg)/mL. On the other hand, the upper limit of the reference value of BNP used in a clinical site is 18.4 pg/mL. Therefore, it has also been confirmed that the method according to the present invention has detection sensitivity capable of measuring, in principle, a BNP value in the vicinity of the upper limit of the reference value of BNP.

Experimental Example 4

Example of BNP Detection Using Clinical Specimen

1) Plasma Preparation

Test subject: Among patients scheduled to undergo a cardiac catheterization test, blood was collected from a patient (#1037) from whom informed consent had been obtained.

Blood collection: Before insertion of a catheter, blood was collected from a catheter sheath, and was dispensed into EDTA-aprotinin blood collection tubes. The BNP value of this patient was 117.1 pg (~33 fmol)/mL.

Treatment after blood collection: The collected blood was stored at 4° C., and plasma separation was performed within 6 hours after blood collection. The resulting plasma was immediately frozen with liquid nitrogen and stored at −80° C. until subjected to analysis.

2) The above-mentioned specimen #1037 was subjected to BNP enrichment in the same manner as in Experimental Example 2.

3) The following samples (k), (l), and (m) were analyzed by mass spectrometry in the same manner as in Experimental Example 2.

Figure 4:
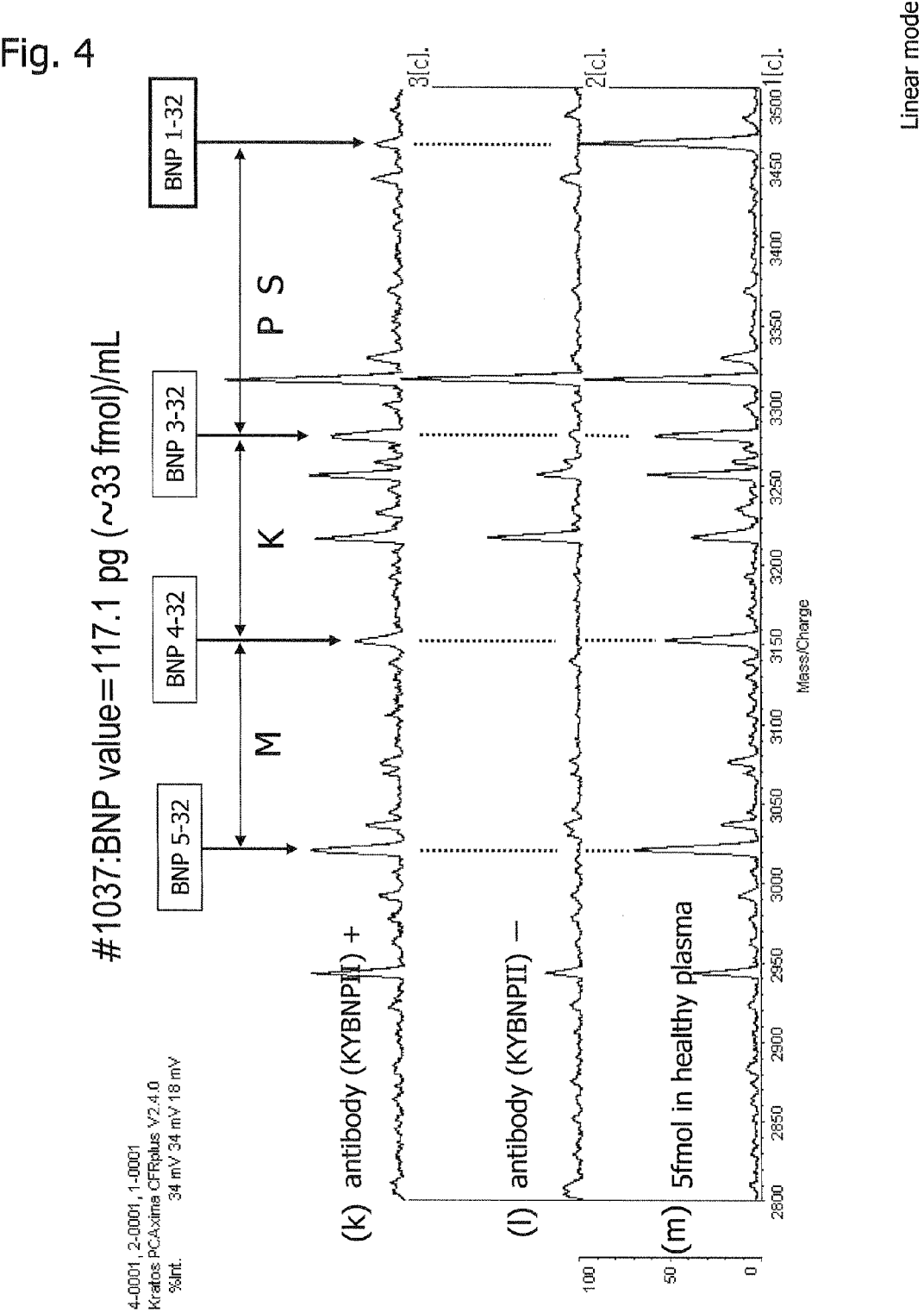
FIG. 4 shows MS spectra obtained in Experimental Example 4, which indicate that BNP 3-32, BNP 4-32, and BNP 5-32 formed from BNP 1-32 by N-terminal processing as well as BNP 1-32 were detected in a clinical specimen.

(k): specimen #1037 subjected to BNP enrichment (l): specimen #1037 not subjected to BNP enrichment (m): sample prepared by adding Mixed BNP (BNP 1-32, BNP 3-32, BNP 4-32, and BNP 5-32; each 5 fmol) to a plasma derived from a healthy person The resulting MS spectra are shown in FIG. 4. As can be seen from FIG. 4(*k*), three specific signals as well as a signal derived from BNP 1-32 were detected. From the results shown in FIGS. 4(*l*) and 4(*m*), it can be considered that these specific signals are derived from BNP 3-32, BNP 4-32, and BNP 5-32 formed by N-terminal processing.

Example 1

Analysis of Plasma in Clinical Specimen

In this example, blood was collected from a patient #1086 (BNP value: 89.0 pg/mL) from whom informed consent had been obtained and from a patient #1067 (BNP value: 92.6 pg/mL) from whom informed consent had been obtained, and the collected blood specimens were subjected to plasma separation, BNP enrichment, and mass spectrometry in the same manner as in Experimental Example 4.

Figure 5:
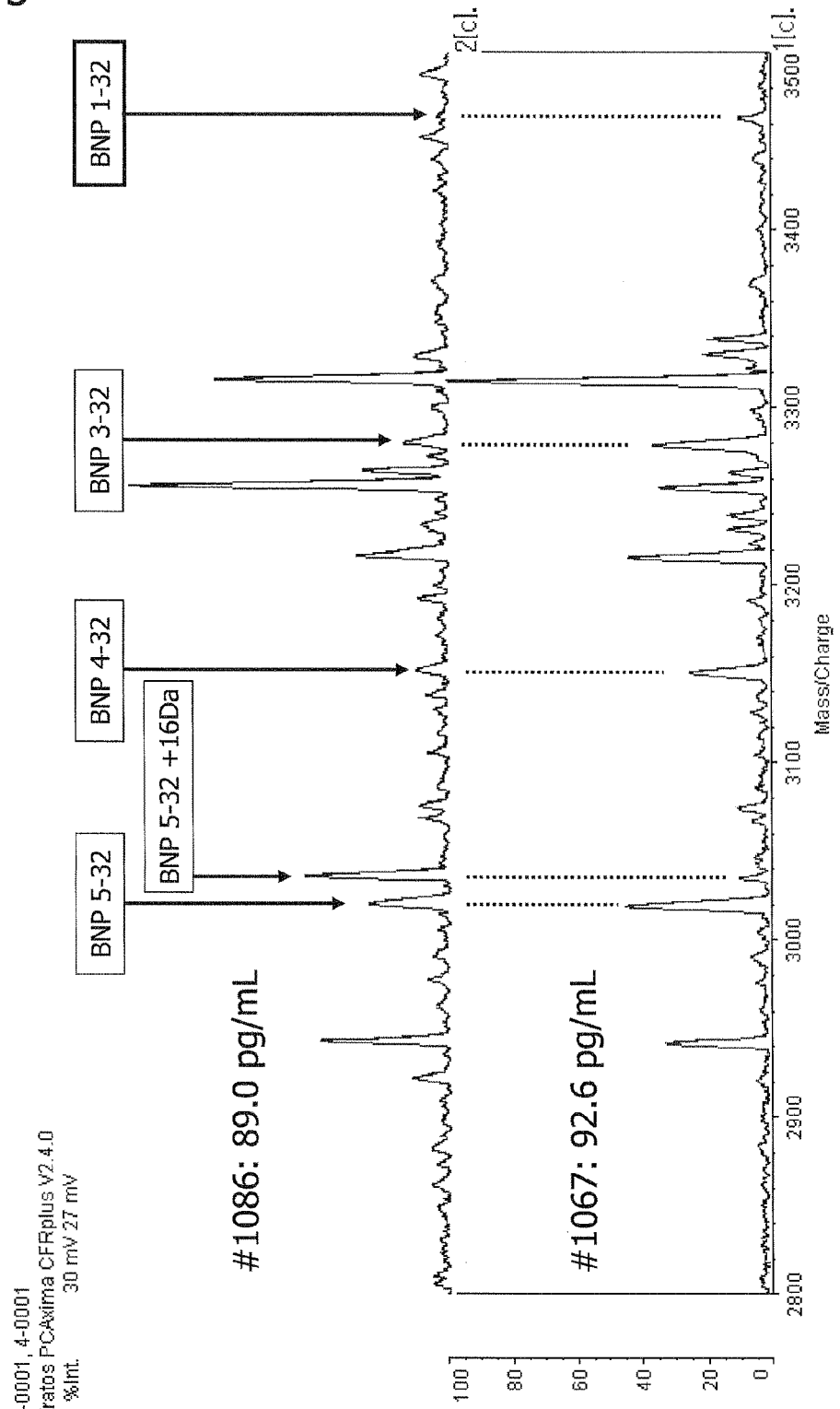
FIG. 5 shows MS spectra obtained in Example 1, which indicate that the method according to the present invention detected a qualitative difference between two plasma specimens prepared from two clinical specimens having almost the same BNP value of about 90 pg/mL as measured by a conventional EIA method.

The resulting MS spectra are shown in FIG. 5. As can be seen from FIG. 5, there is a difference in the pattern of relative intensity ratio of four signals derived from BNP 1-32, BNP 3-32, BNP 4-32, and BNP 5-32 between the patient #1086 and the patient #1067. Also, as can be seen from FIG. 5, when attention is directed toward a signal derived from BNP 5-32 and a signal derived from a molecule having a mass number larger than that of BNP 5-32 by 16 Da, in the case of the patient #1086, the detected intensity of a signal derived from a molecule having a mass number larger than that of BNP 5-32 by 16 Da is higher than that of a signal derived from BNP 5-32, but in the case of the patient #1067, the detected intensity of a signal derived from BNP 5-32 is higher than that of a signal derived from a molecule having a mass number larger than that of BNP 5-32 by 16 Da.

As described above, the BNP values of these two specimens, as measured by a conventional EIA method, are almost the same, that is, about 90 pg/mL. However, according to the method of the present invention, it is possible to detect a qualitative difference between these specimens that cannot be detected by a conventional EIA method.

Example 2

Analysis of MS Signal Patterns and Examination of Correlation Between MS Signal Patterns and Presence or Absence of Significant Stenosis 1-1

In this example, blood was collected from 24 patients from whom informed consent had been obtained, and the collected blood specimens (BNP value: 40.8 pg/mL to 147.8 pg/mL)

were subjected to plasma separation, BNP enrichment, and mass spectrometry in the same manner as in Experimental Example 4.

The relative intensity ratio of a signal derived from a molecule having a mass number larger than that of BNP 5-32 by 16 Da to a signal derived from BNP 5-32 (m/z=3,022) (hereinafter, referred to as "I(BNP 5-32+)/I(BNP 5-32)") was calculated from each of the obtained MS spectra.

The correlation between the values of the ratio and the results of a cardiac catheterization test performed on these patients to determine the presence or absence of significant stenosis was examined. It is to be noted that discrimination between two groups with and without significant stenosis was evaluated by Student's t test (two tailed), and in Example 4 which will be described later, discrimination between the two groups was evaluated by ROC curve analysis.

Figure 6:
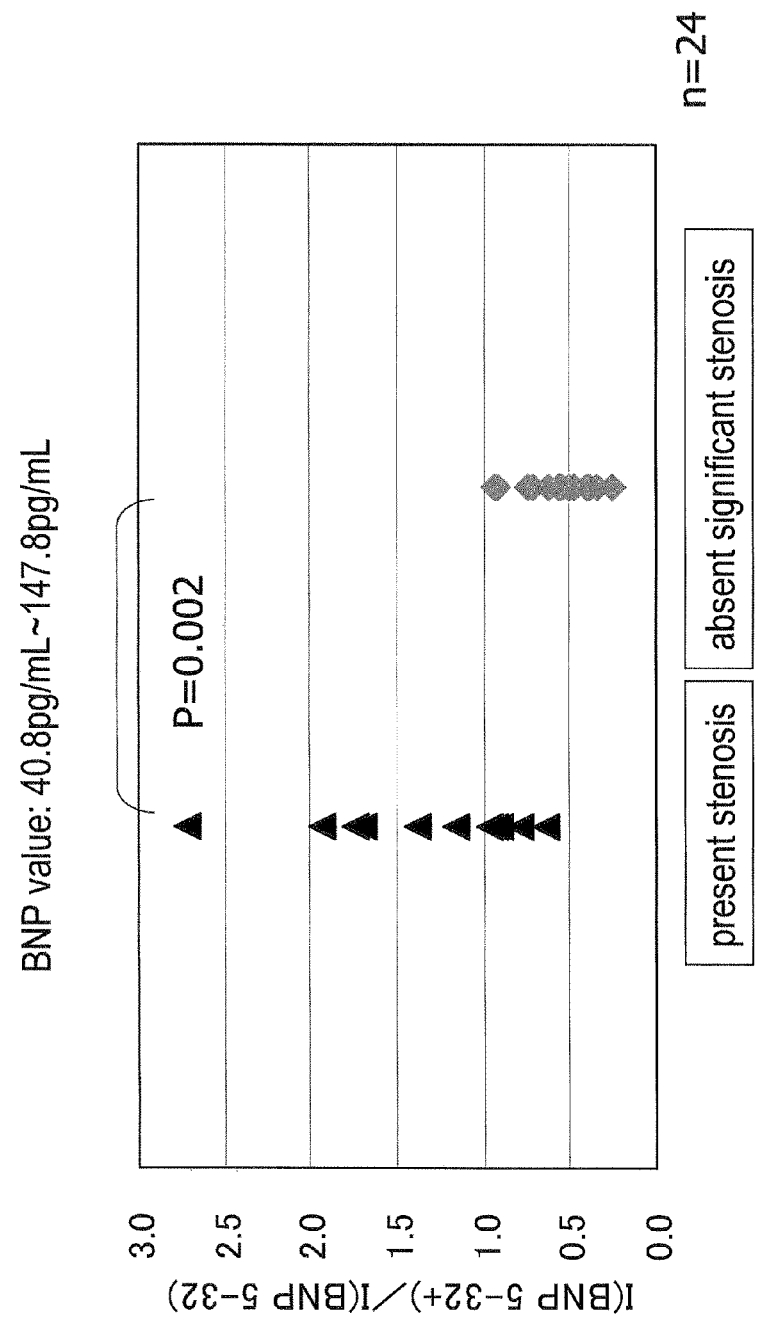
FIG. 6 is a graph obtained in Example 2, which shows the result of analyzing the MS signal patterns regarding 24 clinical specimens whose BNP values were in the range of 40.8 pg/mL to 147.8 pg/mL and examining the correlation between the presence or absence of significant stenosis and an index of I(BNP 5-32+)/I(BNP 5-32).

FIG. 6 shows the relation between the values of I(BNP 5-32+)/I(BNP 5-32) of the 24 patients whose BNP values were in the range of 40.8 pg/mL to 147.8 pg/mL and the presence or absence of significant stenosis.

As shown in FIG. 6, the values of I(BNP 5-32+)/I(BNP 5-32) of the patients diagnosed with significant stenosis were significantly higher (p=0.002) than those of the patients not diagnosed with significant stenosis. That is, in a case where the BNP values of patients were in the range of 40.8 pg/mL to 147.8 pg/mL, there was a remarkable correlation between the values of I(BNP 5-32+)/I(BNP 5-32) of the patients and the presence or absence of significant stenosis.

Example 3

Analysis of MS Signal Patterns and Examination of Correlation Between MS Signal Patterns and Presence or Absence of Significant Stenosis 1-2

In this example, blood was collected from 41 patients from whom informed consent had been obtained, and the MS signal patterns of the collected blood specimens (BNP value: 21.4 pg/mL to 147.8 pg/mL) were analyzed in the same manner as in Example 2 to examine the correlation between the MS signal patterns and the presence or absence of significant stenosis.

Figure 7:
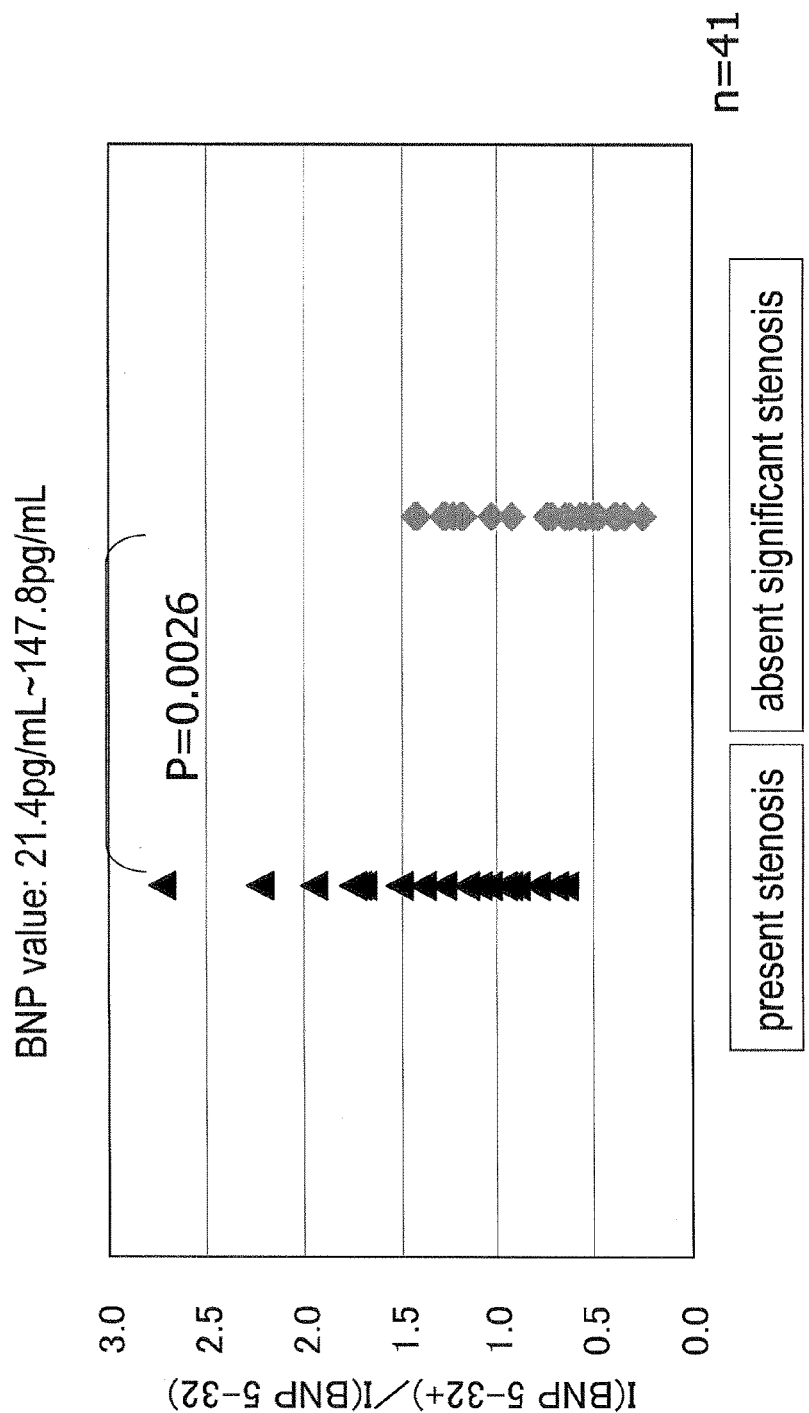
FIG. 7 is a graph obtained in Example 3, which shows the result of analyzing the MS signal patterns regarding 41 clinical specimens whose BNP values were in the range of 21.4 pg/mL to 147.8 pg/mL and examining the correlation, using an index of I(BNP 5-32+)/I(BNP 5-32), between the index and the presence or absence of significant stenosis.

FIG. 7 is a graph showing the relation between the values of I(BNP 5-32+)/I(BNP 5-32) of the 41 patients whose BNP values were 21.4 pg/mL to 147.8 pg/mL and the presence or absence of significant stenosis.

As shown in FIG. 7, the values of I(BNP 5-32+)/I(BNP 5-32) of the patients diagnosed with significant stenosis were significantly higher (p 0.0026) than those of the patients not diagnosed with significant stenosis. That is, also in a case where the BNP values of patients were in the range of 21.4 pg/mL to 147.8 pg/mL, there was a remarkable correlation between the values of I(BNP 5-32+)/I(BNP 5-32) of the patients and the presence or absence of significant stenosis.

Example 4

Analysis of MS Signal Patterns and Examination of Correlation Between MS Signal Patterns and Presence or Absence of Significant Stenosis 1-3

Figure 8:
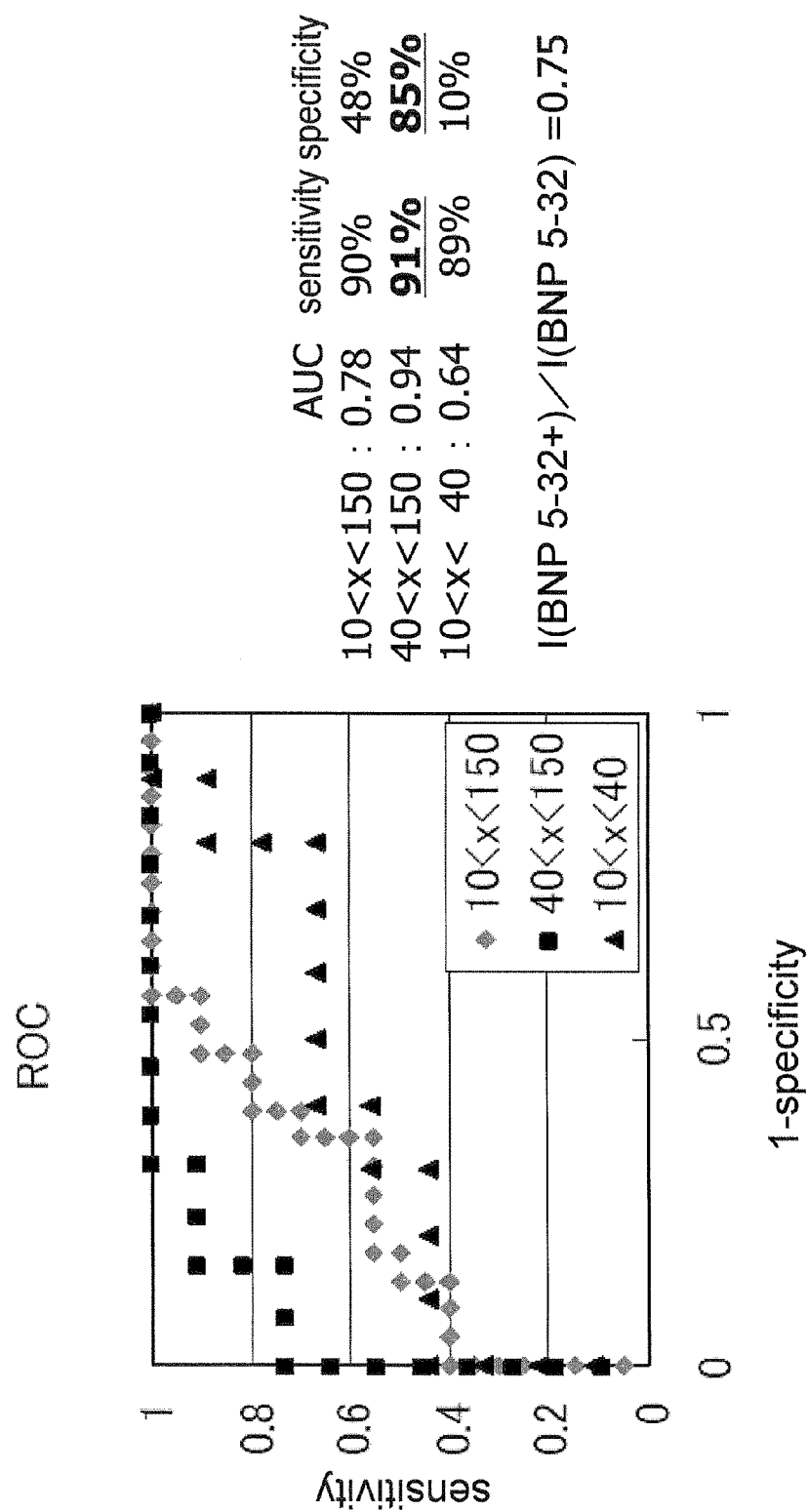
FIG. 8 is a graph obtained in Example 4, which shows the result of analyzing MS signal patterns and examining the correlation between the index of I(BNP 5-32+)/I(BNP 5-32) and the presence or absence of significant stenosis by ROC curve analysis.

In this example, discrimination between two groups with and without significant stenosis was evaluated by ROC curve analysis. FIG. 8 shows ROC curves obtained when the values of BNP "x" (pg/mL) were in the range of 0<x<150, 40<x<150, and 10<x<40. As shown in FIG. 8, a particularly high degree of accuracy was achieved when the of BNP value were in the range of 40<x<150. In this case, the value of AUC was 0.94, and when the value of I(BNP 5-32+)/I(BNP 5-32) was 0.75, the sensitivity and specificity were 91% and 85%, respectively.

Example 5

Analysis of MS Signal Patterns and Examination of Correlation Between MS Signal Patterns and Presence or Absence of Significant Stenosis 2-1

In this example, blood was collected from 33 patients from whom informed consent had been obtained, and the MS signal patterns of the collected blood specimens (BNP value: 21.9 pg/mL to 645.8 pg/mL) were analyzed in the same manner as in Example 2 to examine the correlation between the MS signal patterns and the presence or absence of significant stenosis. It is to be noted that discrimination between two groups was evaluated by Wilcoxon test.

Figure 9:
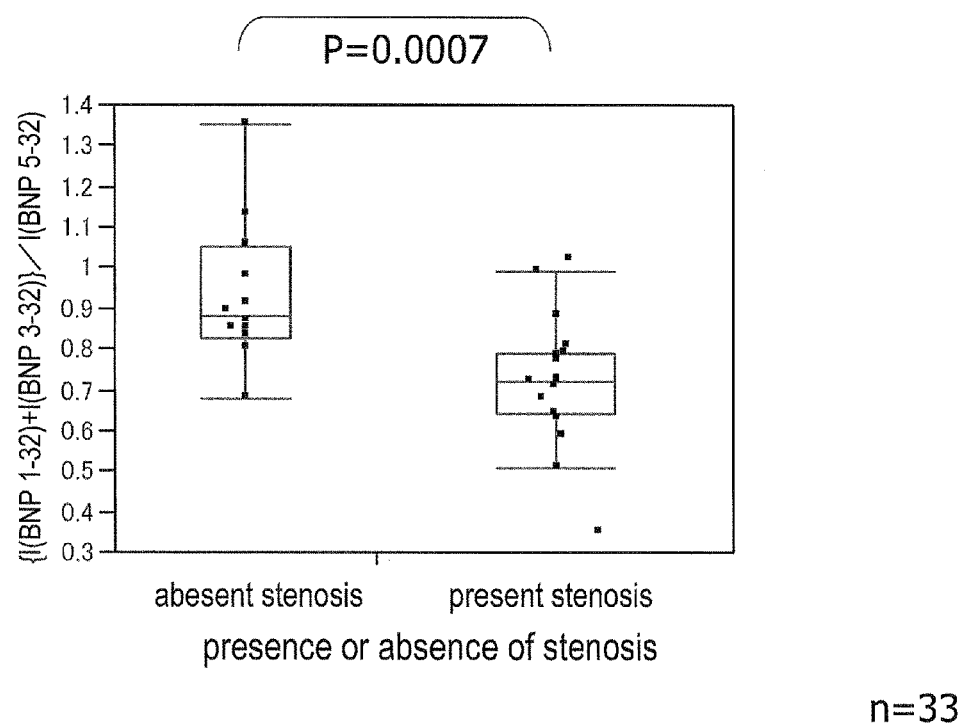
FIG. 9 is a graph obtained in Example 5, which shows the result of analyzing the MS signal patterns regarding 33 clinical specimens whose BNP values were in the range of 21.9 pg/mL to 645.8 pg/mL and examining the correlation, using an index of {I(BNP 1-32)+I(BNP 3-32)/I(BNP 5-32)}, between the index and the presence or absence of significant stenosis.

FIG. 9 is a graph showing the relation between the values of {I(BNP 1-32)+I(BNP 3-32)/I(BNP 5-32)} of the 33 patients whose BNP values were 21.9 to 645.8 pg/mL and the presence or absence of significant stenosis.

As shown in FIG. 9, the values of {I(BNP 1-32)+I(BNP 3-32)/I(BNP 5-32)} of the patients diagnosed with significant stenosis were significantly lower (p=0.0007) than those of the patients not diagnosed with significant stenosis. That is, there was a remarkable correlation between the values of {I(BNP 1-32)+I(BNP 3-32)/I(BNP 5-32)} of the patients diagnosed with significant stenosis and those of the patients not diagnosed with significant stenosis.

Example 6

Analysis of MS Signal Patterns and Examination of Correlation Between MS Signal Patterns and Presence or Absence of Significant Stenosis 2-2

In this example, discrimination between two groups with and without significant stenosis was evaluated by ROC curve analysis. FIG. 10 shows a ROC curve derived from 33 patients whose BNP values were in the range of 21.9 pg/mL to 645.8 pg/mL. As shown in FIG. 10, the value of AUC was 0.85, and when the value of {I(BNP 1-32)+I(BNP 3-32)/I(BNP 5-32)} was 0.79, the sensitivity and specificity were 79% and 93%, respectively.

Comparative Example 1

Analysis of MS Signal Patterns and Examination of Correlation Between MS Signal Patterns and Presence or Absence of Hypertension The correlation between the MS signal patterns of the 33 patients described in Example 5 and the presence or absence of hypertension was examined in the same manner as in Example 5.

FIG. 11 is a graph showing the relation between the values of {I(BNP 1-32)+I(BNP 3-32)/I(BNP 5-32)} of the 33 patients and the presence or absence of hypertension.

As shown in FIG. 11, there was no significant difference (p=0.8411) in the value of {I(BNP 1-32)+I(BNP 3-32)/I(BNP 5-32)} between the patients diagnosed with hypertension (HTN+) and the patients not diagnosed with hypertension (HTN−). That is, unlike the result of Example 5 showing that there is a correlation between the presence or absence of stenosis and the value of the index, the result of Comparative Example 1 shows that there is no correlation between the presence or absence of hypertension and the value of the index.

Comparative Example 2

Analysis of MS Signal Patterns and Examination of Correlation Between MS Signal Patterns and Presence or Absence of Hyperlipidemia The correlation between the MS signal patterns of the 33 patients described in Example 5 and the presence or absence of hyperlipidemia was examined in the same manner as in Example 5.

FIG. 12 is a graph showing the relation between the values of {I(BNP 1-32)+I(BNP 3-32)/I(BNP 5-32)} of the 33 patients and the presence or absence of hyperlipidemia.

As shown in FIG. 12, there was no significant difference (P=0.7680) in the value of {I(BNP 1-32)+I(BNP 3-32)/I(BNP 5-32)} between the patients diagnosed with hyperlipidemia (HL+) and the patients not diagnosed with hypertension (HL−). That is, unlike the result of Example 5 showing that there is a correlation between the presence or absence of stenosis and the value of the index, the result of Comparative Example 2 shows that there is no correlation between the presence or absence of hyperlipidemia and the value of the index.

Comparative Example 3

Analysis of MS Signal Patterns and Examination of Correlation Between MS Signal Patterns and Presence or Absence of Diabetes The correlation between the MS signal patterns of the 33 patients described in Example 5 and the presence or absence of diabetes was examined in the same manner as in Example 5.

FIG. 13 is a graph showing the relation between the values of {I(BNP 1-32)+I(BNP 3-32)/I(BNP 5-32)} of the 33 patients and the presence or absence of diabetes.

As shown in FIG. 13, there was no significant difference (P=0.5712) in the value of {I(BNP 1-32)+I(BNP 3-32)/I(BNP 5-32)} between the patients diagnosed with diabetes (DM+) and the patients not diagnosed with diabetes (DM−). That is, unlike the result of Example 5 showing that there is a correlation between the presence or absence of stenosis and the value of the index, the result of Comparative Example 3 shows that there is no correlation between the presence or absence of diabetes and the value of the index.

Comparative Example 4

Analysis of MS Signal Patterns and Examination of Correlation Between MS Signal Patterns and Gender The correlation between the MS signal patterns of the 33 patients described in Example 5 and gender was examined in the same manner as in Example 5.

FIG. 14 is a graph showing the relation between the values of {I(BNP 1-32)+I(BNP 3-32)/I(BNP 5-32)} of the 33 patients and gender.

As shown in FIG. 14, there was no significant difference (P=0.5383) in the value of {I(BNP 1-32)+I(BNP 3-32)/I(BNP 5-32)} between males (M) and females (F). That is, unlike the result of Example 5 showing that there is a correlation between the presence or absence of stenosis and the value of the index, the result of Comparative Example 4 shows that there is no correlation between gender and the value of the index.

As can be seen from the results of Comparative Examples 1 to 4 and Example 5, the index used in the present invention specifically shows a correlation with the presence or absence of stenosis, but does not show a correlation with the presence or absence of hypertension, hyperlipidemia, and diabetes nor with gender.

Example 7

Analysis of MS Signal Patterns and Examination of Correlation Between MS Signal Patterns and Presence or Absence of Significant Stenosis 3

Analysis of MS signal patterns and examination of correlation between the patterns and the presence or absence of significant stenosis were performed in the same manner as in Example 5 except that the index was changed to I(BNP 4-32)/I(BNP 5-32). The result is shown in FIG. 15. As shown in FIG. 15, the p-value of the index between the patients diagnosed with significant stenosis and the patients not diagnosed with significant stenosis was 0.0771.

Example 8

Analysis of MS Signal Patterns and Examination of Correlation Between MS Signal Patterns and Presence or Absence of Significant Stenosis 4

Analysis of MS signal patterns and examination of correlation between the patterns and the presence or absence of significant stenosis were performed in the same manner as in Example 5 except that the index was changed to {I(BNP 1-32)+I(BNP 3-32)/I(BNP 4-32)}. The result is shown in FIG. 16. As shown in FIG. 16, the p-value of the index between the patients diagnosed with significant stenosis and the patients not diagnosed with significant stenosis was 0.3820.

The foregoing examples are provided to illustrate specific embodiments within the scope of the present invention, but the present invention is not limited thereto and may be embodied in various other forms. For example, the foregoing examples demonstrate that the index used in the present invention is effective when mass spectrometry is used as a detection method, from which it is clear that the same effects can be achieved when a method based on bio-specific affinity is used as a detection method. The foregoing examples are merely illustrative in all aspects including the above aspect and should not be construed as being restrictive. Further, the changes that fall within the equivalents of the claims are all within the scope of the present invention.

INDUSTRIAL APPLICABILITY

According to the present invention, it is possible to less-invasively assess a disease state caused by myocardial ischemia (e.g., ischemic heart disease or restenosis).

Further, according to the present invention, it is possible to determine the presence or absence of cardiovascular disease even from a blood sample having a BNP value from which the presence or absence of cardiovascular disease cannot be determined and only an ambiguous determination that there is suspicion of some kind of cardiovascular disease is made by a conventional method (i.e., a BNP value in the range between the thresholds (18.4 pg/mL to 150 pg/mL) for determining whether there is suspicion of heart failure).

The effects of the present invention will be described more specifically below.

The method according to the present invention uses not a conventional index based on the quantity of BNP (i.e., BNP value) but an index based on the quality of BNP. This makes it possible to obtain, from a blood sample, information that cannot be obtained only from the index based on the quantity of BNP. That is, the present invention makes it possible for the first time to assess myocardial ischemia only through a blood test.

As described above, since the method according to the present invention uses a novel index, it is possible to assess a cardiac disease state even from a blood sample having a BNP value in the range of 18.4 pg/mL to 150 pg/mL from which a cardiac disease state cannot be clearly assessed through a conventional blood test. Further, the effectiveness of the novel index used in the present invention is specific to ischemia, and therefore the presence or absence of myocardial ischemia also in a patient with a disease associated with a high BNP value (e.g., chronic heart failure) can be determined.

The method according to the present invention is applied to a blood test, and is therefore much easier and less invasive than a conventional invasive examination method (e.g., a cardiac catheterization test). Therefore, for the sake of higher accuracy, it is only necessary to perform an invasive test on only patients diagnosed as possibly having stenosis by a previously-performed blood test. This makes it possible to avoid an unnecessary cardiac catheterization test, thereby significantly reducing a burden on the body of a patient and test cost. A cardiac catheterization test is conventionally performed about every six months, and therefore even when restenosis requiring treatment occurs within six months, it is impossible to appropriately treat restenosis. However, the less-invasive blood test can be easily and repeatedly performed, and therefore restenosis can be appropriately treated earlier.

Thus, according to the method of the present invention, unlike a conventional examination method, ischemia can be reliably assessed and early detected only through an easy, less-invasive, and economic blood test. Eventually, the method according to the present invention can be applied to the assessment of arteriosclerosis. Further, as described above, the significance of BNP in a blood sample having a BNP value, from which a cardiac disease state cannot be accurately assessed through a conventional blood test, has become apparent, and therefore there is a possibility that BNP fragments and modified fragments thereof assist drug discovery.

The invention claimed is:

1. A method for assessing coronary restenosis in a test subject after percutaneous coronary intervention (PCI) based on a ratio between specific B-type natriuretic hormone (BNP) molecules, the method comprising:
immunologically enriching a B-type natriuretic hormone (BNP) molecular group containing BNP 1-32 molecule (SEQ ID No. 1), BNP 3-32 molecule (SEQ ID No. 2), and BNP 5-32 molecule (SEQ ID No. 4) from a blood sample obtained from the test subject at a time after PCI by contacting the blood sample with a solid phase-immobilized or -immobilizable antibody specific for the BNP molecular group to form an immobilized immune complex, wherein the antibody is KYBNPII anti-BNP monoclonal antibody,
isolating the immobilized immune complex from other components of the blood sample,
eluting the BNP molecular group from the isolated immune complex,
detecting levels of the BNP 1-32 molecule (SEQ ID No. 1), the BNP 3-32 molecule (SEQ ID No. 2), and the BNP-5-32 molecule (SEQ ID No. 4) in the eluate,
thereby distinguishing and quantifying the individual BNP molecules different in mass number in the blood sample,
calculating a ratio between a sum of the detected level of the BNP 1-32 molecule and the detected level of the BNP 3-32 molecule, to the detected level of the BNP 5-32 molecule, and
assessing coronary restenosis after PCI in the test subject based on the calculated ratio, wherein a ratio lower than that in control test subjects without restenosis is indicative of coronary restenosis after PCI in the test subject.

2. The method according to claim 1, wherein the blood sample is a blood specimen itself of the test subject obtained at a time after PCI having a measured value of BNP of 18 pg/mL to 150 pg/mL, or is prepared from the blood specimen.

3. The method of claim 1, wherein immunologically enriching is by immunoprecipitation or affinity column chromatography.

4. A method for assessing coronary restenosis in a test subject after percutaneous coronary intervention (PCI) based on a ratio between specific B-type natriuretic hormone (BNP) molecules, the method comprising:
immunologically enriching a B-type natriuretic hormone (BNP) molecular group containing BNP 5-32 molecule (SEQ ID No. 4) and a molecule having a mass number larger than that of BNP 5-32 molecule by 16 Da from a blood sample obtained from the test subject at a time after PCI by contacting the blood sample with a solid phase-immobilized or -immobilizable antibody specific for the BNP molecular group to form an immobilized immune complex, wherein the antibody is KYBNPII anti-BNP monoclonal antibody,
isolating the immobilized immune complex from other components of the blood sample,
eluting the BNP molecular group from the isolated immune complex,
detecting levels of the BNP 5-32 molecule (SEQ ID No. 4) and the molecule having a mass number larger than that of the BNP 5-32 molecule by 16 Da in the eluate, thereby distinguishing and quantifying the individual BNP molecules different in mass number in the blood sample,
calculating a ratio between the detected level of the molecule having a mass number larger than that of the BNP 5-32 molecule by 16D to the detected level of the BNP-5-32 molecule, and
assessing coronary restenosis after PCI in the test subject based on the calculated ratio, wherein a ratio higher than that in control test subjects without restenosis is indicative of coronary restenosis after PCI in the test subject.

5. The method according to claim 4, wherein the blood sample is a blood specimen itself of the test subject obtained at a time after PCI having a measured value of BNP of 18 pg/mL to 150 pg/mL, or is prepared from the blood specimen.

6. The method of claim 4, wherein immunologically enriching is by immunoprecipitation or affinity column chromatography.

* * * * *